United States Patent
Li et al.

(10) Patent No.: US 12,276,713 B2
(45) Date of Patent: Apr. 15, 2025

(54) QUAD-CORE RADIO-FREQUENCY COIL CIRCUIT

(71) Applicant: SHENZHEN INSTITUTES OF ADVANCED TECHNOLOGY, Nanshan Shenzhen (CN)

(72) Inventors: Ye Li, Nanshan Shenzhen (CN); Feng Du, Nanshan Shenzhen (CN); Nan Li, Nanshan Shenzhen (CN); Xing Yang, Nanshan Shenzhen (CN); Qiaoyan Chen, Nanshan Shenzhen (CN); Xin Liu, Nanshan Shenzhen (CN); Hairong Zheng, Nanshan Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 241 days.

(21) Appl. No.: 17/921,465

(22) PCT Filed: Jul. 23, 2020

(86) PCT No.: PCT/CN2020/103680
§ 371 (c)(1),
(2) Date: Oct. 26, 2022

(87) PCT Pub. No.: WO2021/217910
PCT Pub. Date: Nov. 4, 2021

(65) Prior Publication Data
US 2023/0204697 A1 Jun. 29, 2023

(30) Foreign Application Priority Data
Apr. 27, 2020 (CN) .......... 202010346493.X

(51) Int. Cl.
*G01R 33/36* (2006.01)
*G01R 33/3415* (2006.01)

(52) U.S. Cl.
CPC ..... *G01R 33/3635* (2013.01); *G01R 33/3415* (2013.01)

(58) Field of Classification Search
CPC .................. G01R 33/3415; G01R 33/3635
See application file for complete search history.

(56) References Cited

U.S. PATENT DOCUMENTS 8,049,501 B2 * 11/2011 Hancu ............... G01R 33/3678
324/318
9,606,204 B2 3/2017 Qiu et al.
(Continued)

FOREIGN PATENT DOCUMENTS

CN 1420363 A 5/2003
CN 101427150 A 5/2009
(Continued)

OTHER PUBLICATIONS

Machine Translation of CN107329100A (Year: 2017).*
(Continued)

*Primary Examiner* — Gregory H Curran
(74) *Attorney, Agent, or Firm* — Woodard, Emhardt, Henry, Reeves & Wagner, LLP

(57) ABSTRACT

Provided is a quad-core radio-frequency coil circuit. The quad-core radio-frequency coil circuit includes a coil module (1) and a front-end module (2). The coil module (1) is configured to receive a nuclear magnetic test signal and, according to the nuclear magnetic test signal, generate an induction signal. The front-end module (2) is connected to the coil module (1) and configured to generate the nuclear magnetic test signal and collect the induction signal.

12 Claims, 16 Drawing Sheets

(56) References Cited

U.S. PATENT DOCUMENTS

| | | | |
|---|---|---|---|
| 2003/0122546 A1* | 7/2003 | Leussler | G01R 33/341 324/318 |
| 2013/0314088 A1* | 11/2013 | Wiggins | G01R 33/3635 324/322 |
| 2019/0020227 A1 | 1/2019 | Umemori | |

FOREIGN PATENT DOCUMENTS

| | | |
|---|---|---|
| CN | 102293649 | 12/2011 |
| CN | 102762997 A | 10/2012 |
| CN | 105759230 A | 7/2016 |
| CN | 106842087 | 6/2017 |
| CN | 107329100 A | 11/2017 |
| CN | 107526049 A | 12/2017 |
| CN | 107561464 A | 1/2018 |
| CN | 108680882 A | 10/2018 |
| CN | 111426997 A | 7/2020 |
| CN | 212433380 | 1/2021 |

OTHER PUBLICATIONS

International Search Report of PCT/CN2020/103680 mailed Jan. 29, 2021.
Office Action in related China 202010346493X mailed Nov. 1, 2024.
Search Report in related China 202010346493X mailed Nov. 1, 2024.

* cited by examiner

QUAD-CORE RADIO-FREQUENCY COIL CIRCUIT

CROSS-REFERENCE TO RELATED APPLICATIONS

This is a National Stage Application filed under 35 U.S.C. 371 based on International Patent Application No. PCT/CN2020/103680, filed on Jul. 23, 2020, which claims priority to Chinese Patent Application No. 202010346493.X filed on Apr. 27, 2020, the disclosures of both of which are incorporated herein by reference in their entireties.

TECHNICAL FIELD

Embodiments of the present application relate to nuclear magnetic resonance technology and, for example, a quad-core radio-frequency coil circuit.

BACKGROUND

In the related art, hydrogen atom magnetic resonance imaging has been relatively mature, but only hydrogen atom imaging has not been able to meet the need of humans for the diagnosis of various diseases. Since multinuclear magnetic resonance imaging technology can be used for obtaining morphological and metabolic information in a biological system, the multinuclear magnetic resonance imaging technology has been rapidly developed. In addition to hydrogen-1 (1H), there are studies of nuclides such as carbon-13 (13C), fluorine-19 (19F), sodium-23 (23Na), and phosphorus-31 (31P). With the development of magnetic resonance technology, three-tuned magnetic resonance radio-frequency probes or coils have been proposed to meet the need for detecting three different magnetic resonance (MR) sensitive nuclei. In the related art, the lumped element technology is used to demonstrate this design in small coils, and the feasibility of this design in triple-frequency operation for small sample MR imaging applications is displayed. However, due to the complex structure of a multi-tuned coil, the difficulty in the design, manufacturing, and debugging of the multi-tuned coil is greatly increased. There is no multi-channel radio-frequency coil system for implementing synchronous excitation and collection of four-nuclide signals in the high field and the ultra-high field in the related art. In large sample imaging applications with high magnetic fields, a multi-channel quad-core radio-frequency (RF) coil may encounter technical challenges. The interaction between different core channels, the mutual coupling between channels, and complex electromagnetic wave behavior, dielectrics and conductive biological samples in high intensity electromagnetic fields can severely reduce the transmission efficiency and reception sensitivity of the coil. In the radio frequency technology, to have uniform excitation when exciting signals, there is a receiving field with high sensitivity when receiving the signals. Quadrature excitation of multi-nuclide multi-channel coils is implemented by changing phases of excitation sources of different channels to generate a circularly polarized emission field. A high sensitivity receiving field is formed in a receiving mode to have sufficient coverage to improve the signal-to-noise ratio (SNR) of weak nuclides.

In a variety of configurations of dual-core RF coils for observing signals from nuclei other than protons (for example, 19F and 31P), a dual-tuned coil design may be implemented by using a common-mode and differential-mode method or using two geometrically isolated coils (B1 fields perpendicular to each other). The preceding methods are generally used for a single-core quadrature coil design to improve SNR, but the coil can also be used as a dual resonance mode without using a quadrature configuration. For example, one of two coils may be a loop tuned to 1H, and another coil may be a butterfly, dual-loop, or monopole antenna tuned to another core or a tuned microstrip transmission line. Two independent coil loops may be nested and combined to form a dual resonance unit. A dual-core resonance coil unit sharing one coil loop is implemented by inserting a resonance network at the coil port. Most multi-nuclear magnetic resonance experiments are performed by separately performing mononuclear image collection and then registering images collected from each nucleus. This is not only time-consuming, but also it is difficult to successfully complete image registration because coil settings and image resolution for image collection by each nucleus are different. One solution is to use multiple tuned coil arrays to detect multicore signals simultaneously. However, the design of this coil is complex, and the interaction and crosstalk between individually tuned coil elements must be suppressed.

SUMMARY

The present application provides a quad-core radio-frequency coil circuit to implement multi-channel, multi-frequency, and high-uniformity radio-frequency excitation and high sensitivity signal collection. The quad-core radio-frequency coil circuit includes a coil module and a front-end module.

The coil module is configured to receive a nuclear magnetic test signal and, according to the nuclear magnetic test signal, generate an induction signal.

The front-end module is connected to the coil module and configured to generate the nuclear magnetic test signal and collect the induction signal.

Optionally, the coil module includes a first coil array and a second coil array. The center position of the first coil array coincides with the center position of the second coil array.

Optionally, the first coil array includes a first sub-coil array and a second sub-coil array. The first sub-coil array includes a plurality of first coil units. The plurality of first coil units are superimposed based on a first preset phase difference. The second sub-coil array includes a plurality of second coil units. The plurality of second coil units are superimposed based on a second preset phase difference. The second coil array includes a plurality of third coil units. The plurality of third coil units are superimposed based on a third preset phase difference.

Optionally, a first coil unit includes a first interface circuit and a first detuning circuit. The first detuning circuit is connected to the first interface circuit. The first interface circuit is connected to the front-end module.

Optionally, the first interface circuit includes an input end IN1, an input end IN2, a capacitor C1, a capacitor C2, and an inductor L1. The input end IN1 is connected to a first end of the capacitor C1. A second end of the capacitor C1 is connected to a first end of the capacitor C2. A second end of the capacitor C2 is connected to a first end of the inductor L1. A second end of the inductor L1 is connected to the first end of the capacitor C2. The input end IN2 is connected to the second end of the capacitor C1.

Optionally, the first detuning circuit includes an inductor L2, an inductor L3, an inductor L4, an inductor L5, a capacitor C3, a capacitor C4, a capacitor C5, a diode D1, a diode D2, and a diode D3. A first end of the inductor L2 is connected to a first end of the capacitor C3. A second end of the inductor L2 is connected to a negative electrode of the diode D1. A positive electrode of the diode D1 is connected to a second end of the capacitor C3. A second end of the capacitor C4 is connected to the first end of the capacitor C3. A positive electrode of the diode D2 is connected to the second end of the capacitor C4. A negative electrode of the diode D2 is connected to a second end of the inductor L3. A first end of the inductor L3 is connected to a first end of the capacitor C4. A second end of the capacitor C5 is connected to the first end of the capacitor C4. A positive electrode of the diode D3 is connected to the second end of the capacitor C5. A negative electrode of the diode D3 is connected to a second end of the inductor L4. A first end of the inductor L4 is connected to a first end of the capacitor C5. A first end of the inductor L5 is connected to the second end of the capacitor C5. A second end of the inductor L5 is connected to the first end of the capacitor C4. Alternatively, a first end of the inductor L2 is connected to a first end of the capacitor C3. A second end of the inductor L2 is connected to a negative electrode of the diode D1. A positive electrode of the diode D1 is connected to a second end of the capacitor C3. A second end of the capacitor C4 is connected to the second end of the capacitor C3. A positive electrode of the diode D2 is connected to a first end of the capacitor C4. A negative electrode of the diode D2 is connected to a second end of the inductor L3. A first end of the inductor L3 is connected to the second end of the capacitor C4. A positive electrode of the diode D3 is connected to a second end of the capacitor C5. A negative electrode of the diode D3 is connected to a second end of the inductor L4. A first end of the inductor L4 is connected to a first end of the capacitor C5. A first end of the inductor L5 is connected to the first end of the capacitor C5. A second end of the inductor L5 is connected to the first end of the capacitor C4.

Optionally, a second coil unit includes a second interface circuit and a second detuning circuit. The second detuning circuit is connected to the second interface circuit. The second interface circuit is connected to the front-end module.

Optionally, the second interface circuit includes an input end IN1, an input end IN2, a capacitor C6, a capacitor C7, and an inductor L6. The input end IN1 is connected to a first end of the capacitor C6. A second end of the capacitor C6 is connected to a first end of the capacitor C7. A second end of the capacitor C7 is connected to a first end of the inductor L6. A second end of the inductor L6 is connected to the first end of the capacitor C7. The input end IN2 is connected to the second end of the capacitor C6.

Optionally, the second detuning circuit includes an inductor L7, an inductor L8, an inductor L9, an inductor L10, a capacitor C8, a capacitor C9, a capacitor C10, a diode D4, a diode D5, and a diode D6. A first end of the inductor L7 is connected to a first end of the capacitor C8. A second end of the inductor L7 is connected to a negative electrode of the diode D4. A positive electrode of the diode D4 is connected to a second end of the capacitor C8. A second end of the capacitor C9 is connected to the first end of the capacitor C8. A positive electrode of the diode D5 is connected to the second end of the capacitor C9. A negative electrode of the diode D5 is connected to a second end of the inductor L8. A first end of the inductor L8 is connected to a first end of the capacitor C9. A positive electrode of the diode D6 is connected to a second end of the capacitor C10. A negative electrode of the diode D6 is connected to a second end of the inductor L9. A first end of the inductor L9 is connected to a first end of the capacitor C10. A first end of the inductor L10 is connected to the second end of the capacitor C10. A second end of the inductor L10 is connected to the first end of the capacitor C9. Alternatively, a first end of the inductor L7 is connected to a first end of the capacitor C8. A second end of the inductor L7 is connected to a negative electrode of the diode D4. A positive electrode of the diode D4 is connected to a second end of the capacitor C8. A second end of the capacitor C9 is connected to the second end of the capacitor C8. A positive electrode of the diode D5 is connected to a first end of the capacitor C9. A negative electrode of the diode D5 is connected to a second end of the inductor L8. A first end of the inductor L8 is connected to the second end of the capacitor C9. A positive electrode of the diode D6 is connected to a second end of the capacitor C10. A negative electrode of the diode D6 is connected to a second end of the inductor L9. A first end of the inductor L9 is connected to a first end of the capacitor C10. A first end of the inductor L10 is connected to the first end of the capacitor C10. A second end of the inductor L10 is connected to the first end of the capacitor C9.

Optionally, a third coil unit includes a third interface circuit and a third detuning circuit. The third detuning circuit is connected to the third interface circuit. The third interface circuit is connected to the front-end module.

Optionally, the third interface circuit includes an input end IN1, an input end IN2, a capacitor C11, a capacitor C12, a capacitor C13, a capacitor C14, a capacitor C15, a variable capacitor B1, a variable capacitor B2, an inductor L11, an inductor L12, and an inductor L13. The input end IN1 is connected to a first end of the capacitor C11. A second end of the capacitor C11 is connected to a first end of the capacitor C12. A first end of the inductor L13 is connected to a second end of the capacitor C12. A second end of the inductor L13 is connected to the first end of the capacitor C11. A first end of the capacitor C13 is connected to the second end of the capacitor C12. A second end of the capacitor C13 is connected to a first end of the capacitor C14. A second end of the capacitor C14 is connected to a first end of the capacitor C15. A second end of the capacitor C15 is connected to the input end IN2. A first end of the inductor L12 is connected to the second end of the capacitor C11. A second end of the inductor L12 is connected to the second end of the capacitor C15. A first end of the inductor L11 is connected to the first end of the capacitor C14. A second end of the inductor L11 is connected to the second end of the capacitor C15. A first end of the variable capacitor B1 is connected to the first end of the capacitor C13. A second end of the variable capacitor B1 is connected to the second end of the capacitor C13. A first end of the variable capacitor B2 is connected to the first end of the capacitor C12. A second end of the variable capacitor B2 is connected to the second end of the capacitor C15.

Optionally, the third detuning circuit includes a capacitor C16, a capacitor C17, a capacitor C18, a capacitor C19, an inductor L14, an inductor L15, an inductor L16, an inductor L17, a diode D7, a diode D8, and a diode D9. A first end of the inductor L16 is connected to a first end of the capacitor C16. A second end of the inductor L16 is connected to a negative electrode of the diode D7. A positive electrode of the diode D7 is connected to a second end of the capacitor C16. A second end of the capacitor C17 is connected to the first end of the capacitor C16. A first end of the capacitor C17 is connected to a second end of the capacitor C18. A positive electrode of the diode D8 is connected to the second end of the capacitor C17. A negative electrode of the diode D8 is connected to a second end of the inductor L14. A first end of the inductor L14 is connected to a first end of the capacitor C18. A positive electrode of the diode D9 is connected to a second end of the capacitor C19. A negative electrode of the diode D9 is connected to a second end of the inductor L15. A first end of the inductor L15 is connected to a first end of the capacitor C19. A first end of the inductor L17 is connected to the first end of the capacitor C18. A second end of the inductor L17 is connected to the second end of the capacitor C19. Alternatively, a first end of the inductor L16 is connected to a first end of the capacitor C16. A second end of the inductor L16 is connected to a negative electrode of the diode D7. A positive electrode of the diode D7 is connected to a second end of the capacitor C16. A second end of the capacitor C18 is connected to the second end of the capacitor C16. A first end of the capacitor C17 is connected to a first end of the capacitor C18. A positive electrode of the diode D8 is connected to a second end of the capacitor C17. A negative electrode of the diode D8 is connected to a second end of the inductor L14. A first end of the inductor L14 is connected to the second end of the capacitor C18. A positive electrode of the diode D9 is connected to a second end of the capacitor C19. A negative electrode of the diode D9 is connected to a second end of the inductor L15. A first end of the inductor L15 is connected to a first end of the capacitor C19. A first end of the inductor L17 is connected to the first second end of the capacitor C17. A second end of the inductor L17 is connected to the second-first end of the capacitor C19.

Optionally, the front-end module includes a power division module and a signal driver module. The power division module is connected to the signal driver module. The signal driver module is connected to the coil module. The power division module is configured to divide the nuclear magnetic test signal into multiplex test signals. The signal driver module is configured to input the multiplex test signals into the coil module.

DETAILED DESCRIPTION

Figure 1:
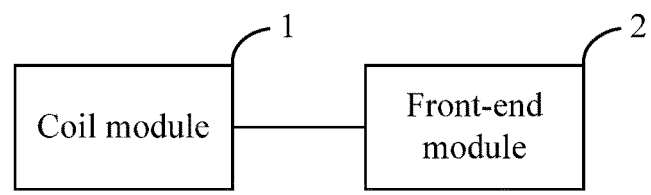
FIG. 1 is a module connection diagram of a quad-core radio-frequency coil circuit according to embodiment one of the present application.

The present application is described below in conjunction with drawings and embodiments. The embodiments described herein are merely intended to explain and not to limit the present application. Only part, not all, of structures related to the present application are illustrated in the drawings.

Before the example embodiments are discussed, it is to be noted that some of the example embodiments are described as processing or methods depicted in flowcharts. Although multiple steps are described as sequential processing in the flowcharts, many of the steps may be implemented concurrently, coincidentally or simultaneously. Additionally, the sequence of the multiple steps may be rearranged. A process may be terminated when operations of the process are completed, but may further have additional steps not included in the drawings. The processing may correspond to a method, a function, a procedure, a subroutine, a subprogram or the like.

Additionally, the terms "first", "second", and the like may be used herein to describe multiple directions, actions, steps, elements, or the like, but these directions, actions, steps, or elements are not limited by these terms. These terms are only used for distinguishing one direction, action, step, or element from another direction, action, step, or element. For example, without departing from the scope of the present application, a first coil array may be referred to as a second coil array, and similarly, the second coil array may be referred to as the first coil array. Both the first coil array and the second coil array are coil arrays, but these are not the same coil array. Terms like "first", "second", and the like are not to be construed as indicating or implying relative importance or implicitly indicating the number of technical features as indicated. Thus, a feature defined as a "first" feature or a "second" feature may explicitly or implicitly include one or more of such features. As described herein, the term "multiple" is defined as at least two, for example, two, three, or the like, unless otherwise expressly limited.

Embodiment One

FIG. 1 is a module connection diagram of a quad-core radio-frequency coil circuit according to embodiment one of the present application. This embodiment is applicable to the case where multiple nuclide signals are used for nuclear magnetic resonance. The quad-core radio-frequency coil circuit according to this embodiment includes a coil module 1 and a front-end module 2.

The coil module 1 is configured to receive a nuclear magnetic test signal and, according to the nuclear magnetic test signal, generate an induction signal. In this embodiment, the nuclear magnetic test signal is generated by an instrument such as a signal generator to perform nuclear magnetic resonance imaging. Common nuclides include 1H (hydrogen), 13C (carbon), 19F (fluorine), 23Na (sodium), and 31P (phosphorus). The quad-core radio-frequency coil circuit provided in this embodiment is described by taking 1H, 19F, 23Na, and 31P as an example. The induction signal is the induction signal fed back by a user according to the nuclear magnetic test signal. After collecting the induction signal fed back by the user, the coil module 1 can transmit the induction signal to an instrument such as an oscilloscope for imaging.

Figure 2:
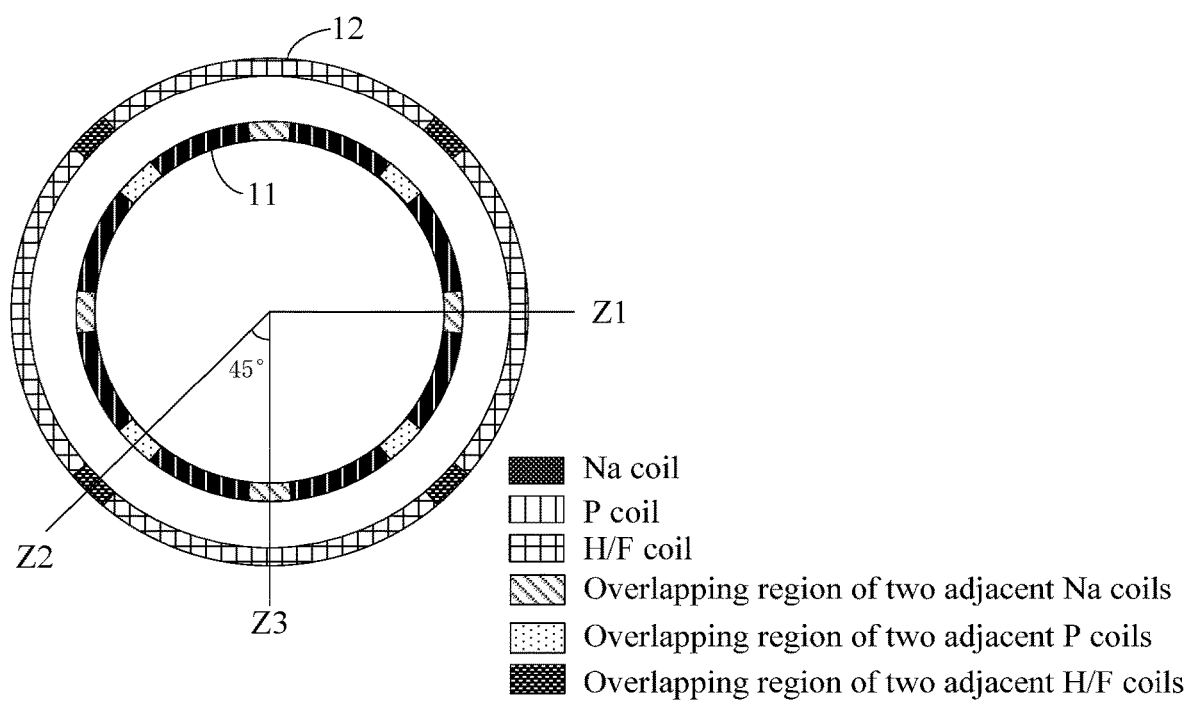
FIG. 2 is a top view illustrating the structure of a quad-core radio-frequency coil circuit according to embodiment one of the present application.

Referring to FIG. 2, the coil module 1 includes a first coil array 11 and a second coil array 12. The center position of the first coil array 11 coincides with the center position of the second coil array 12. FIG. 2 is a top view illustrating the structure of the quad-core radio-frequency coil circuit according to this embodiment. The first coil array 11 and the second coil array 12 are designed through using a double-layer nested structure. The first coil array 11 includes a first sub-coil array and a second sub-coil array. The first sub-coil array includes four Na coils. The second sub-coil array includes four P coils. The four Na coils enclose a circular structure. The four P coils enclose a circular structure. The circular structure enclosed by the four Na coils and the circular structure enclosed by the four P coils have the same radius of the cross section, and the centers of the two circular structures coincide. The second coil array 12 includes four H/F coils. The four H/F coils also enclose a circular structure. The center of the circular structure coincides with the center of the circular structure enclosed by the four Na coils and the center of the circular structure enclosed by the four P coils. Two adjacent Na coils of the four Na coils partially overlap. Two adjacent P coils of the four P coils partially overlap. Two adjacent H/F coils of the four H/F coils partially overlap. The center line of the P coils perpendicular to the plane in which the P coils are located (ignoring the coil radian) coincides with the center line of the H/F coils perpendicular to the plane in which the H/F coils are located, for example, coincides with the axis Z1 passing through the center of the circle. The difference between the center line Z2 of the Na coils perpendicular to the plane in which the Na coils are located (ignoring the coil radian) and the center line Z3 of the H/F coils perpendicular to the plane in which the H/F coils are located (ignoring the coil radian) is 45°. The position of the center line Z2 of the Na coils is shifted by 45° relative to the position of the center line Z3 of the H/F coils, thereby solving the problem that the inner and outer coil arrays interfere with each other.

The Na coils are coils whose frequencies are tuned to 23Na. The P coils are coils whose frequencies are tuned to 31P. The H/F coils are coils whose frequencies are tuned to 1H and 19F.

Figure 3:
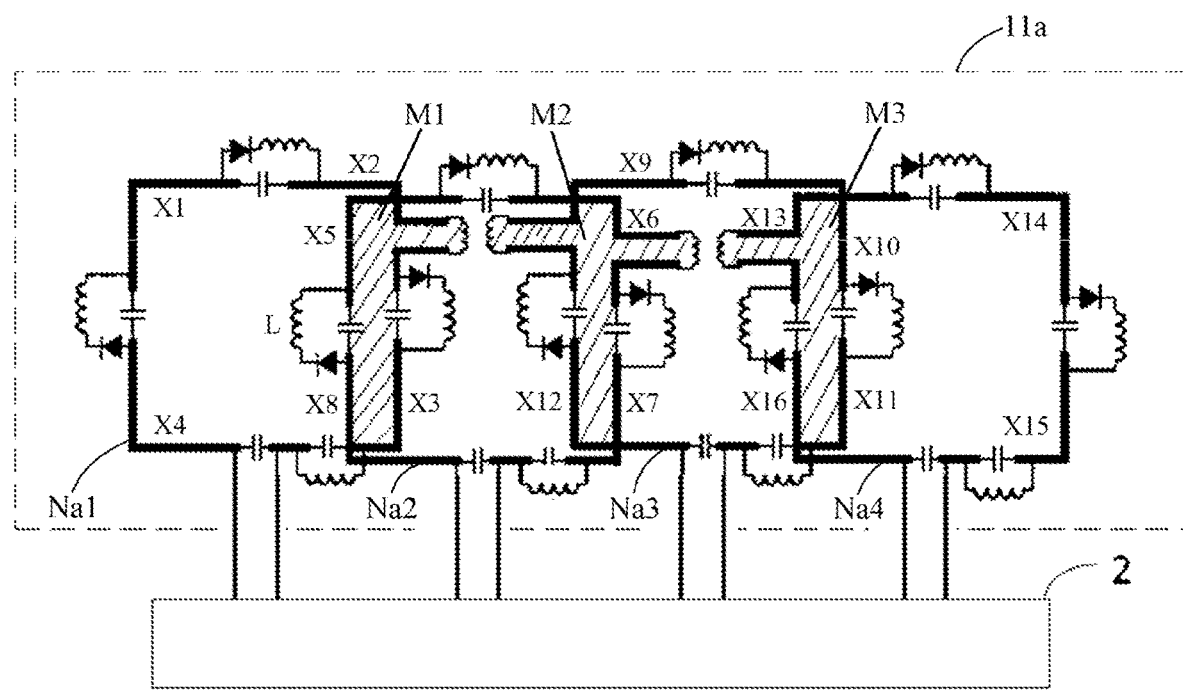
FIG. 3 is a circuit diagram of a first sub-coil array according to embodiment one of the present application.

Referring to FIG. 3, FIG. 3 is a circuit diagram of a first sub-coil array 11a. In this embodiment, the first sub-coil array 11a is described by taking four Na coils as an example. The first sub-coil array 11a includes multiple first coil units (a coil Na1, a coil Na2, a coil Na3, and a coil Na4). The multiple first coil units are superimposed based on a first preset phase difference. The coil Na1, the coil Na2, the coil Na3, and the coil Na4 are Na coils. The wires X2 and X3 of the coil Na1 and the wires X5 and X8 of the coil Na2 enclose an overlapping region M1 with area A1. The wires X6 and X7 of the coil Na2 and the wires X9 and X12 of the coil Na3 enclose an overlapping region M2 with area A2. The wires X10 and X11 of the coil Na3 and the wires X13 and X16 of the coil Na4 enclose an overlapping region M3 with area A3. By superimposing the multiple first coil units in the first sub-coil array 11a, the effect of decoupling adjacent coil channels is implemented, and the interference between the Na coils is reduced.

Figure 4:
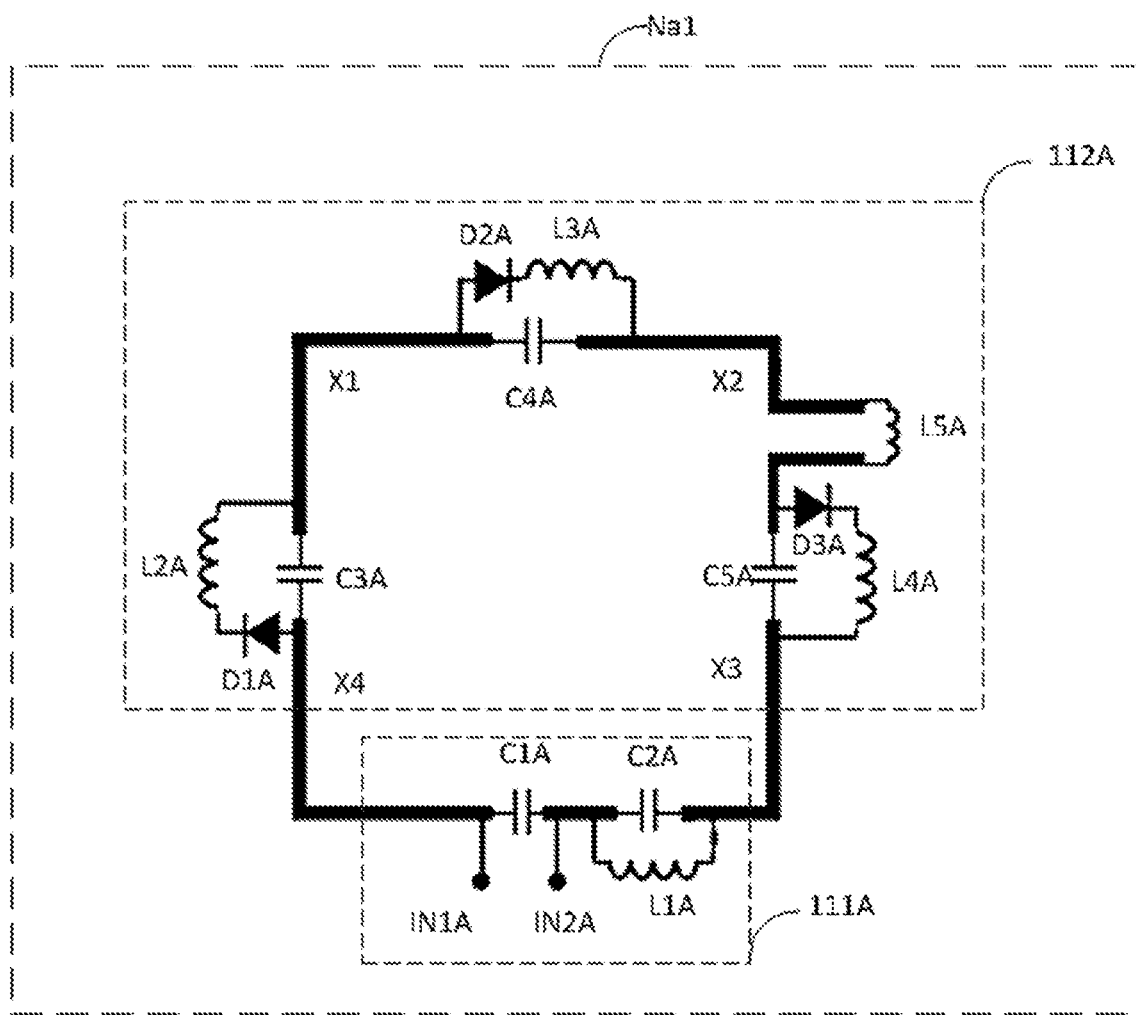
FIG. 4 is a circuit diagram of a coil Na1 according to embodiment one of the present application.

Referring to FIG. 4, the coil Na1 in the first coil units includes a first interface circuit 111A and a first detuning circuit 112A. The first detuning circuit 112A is connected to the first interface circuit 111A. The first interface circuit 111A is connected to the front-end module 2. The wires X1, X2, X3, and X4 of the coil Na1 enclose a rectangle with a raised structure. The wire X1, the wire X3, and the wire X4 are L-shaped wires. The wire X2 includes a Z-shaped wire and an L-shaped wire. The raised structure is formed between the Z-shaped wire and the L-shaped wire to connect an inductor L5A. A secondary detuning circuit composed of an inductor L2A, a diode D1A, and a capacitor C3A is connected between the wire X1 and the wire X4. A secondary detuning circuit composed of an inductor L3A, a diode D2A, and a capacitor C4A is connected between the wire X1 and the wire X2. A secondary detuning circuit composed of an inductor L4A, a diode D3A, and a capacitor C5A is connected between the wire X2 and the wire X3. The first interface circuit 111A is connected between the wire X4 and the wire X3. FIG. 4 is a circuit diagram of the coil Na1. The first interface circuit 111A includes an input end IN1A, an input end IN2A, a capacitor C1A, a capacitor C2A, and an inductor L1A. The input end IN1A is connected to a first end of the capacitor C1A. A second end of the capacitor C1A is connected to a first end of the capacitor C2A. A second end of the capacitor C2A is connected to a first end of the inductor L1A. A second end of the inductor L1A is connected to the first end of the capacitor C2A. The input end IN2A is connected to the second end of the capacitor C1A. The first detuning circuit 112A includes the inductor L2A, the inductor L3A, the inductor L4A, the inductor L5A, the capacitor C3A, the capacitor C4A, the capacitor C5A, the diode D1A, the diode D2A, and the diode D3A. A first end of the inductor L2A is connected to a first end of the capacitor C3A. A second end of the inductor L2A is connected to a negative electrode of the diode D1A. A positive electrode of the diode D1A is connected to a second end of the capacitor C3A. A second end of the capacitor C4A is connected to the first end of the capacitor C3A. A positive electrode of the diode D2A is connected to the second end of the capacitor C4A. A negative electrode of the diode D2A is connected to a second end of the inductor L3A. A first end of the inductor L3A is connected to a first end of the capacitor C4A. A positive electrode of the diode D3A is connected to a second end of the capacitor C5A. A negative electrode of the diode D3A is connected to a second end of the inductor L4A. A first end of the inductor L4A is connected to a first end of the capacitor C5A. A first end of the inductor L5A is connected to the second end of the capacitor C5A. A second end of the inductor L5A is connected to the first end of the capacitor C4A.

Figure 5:
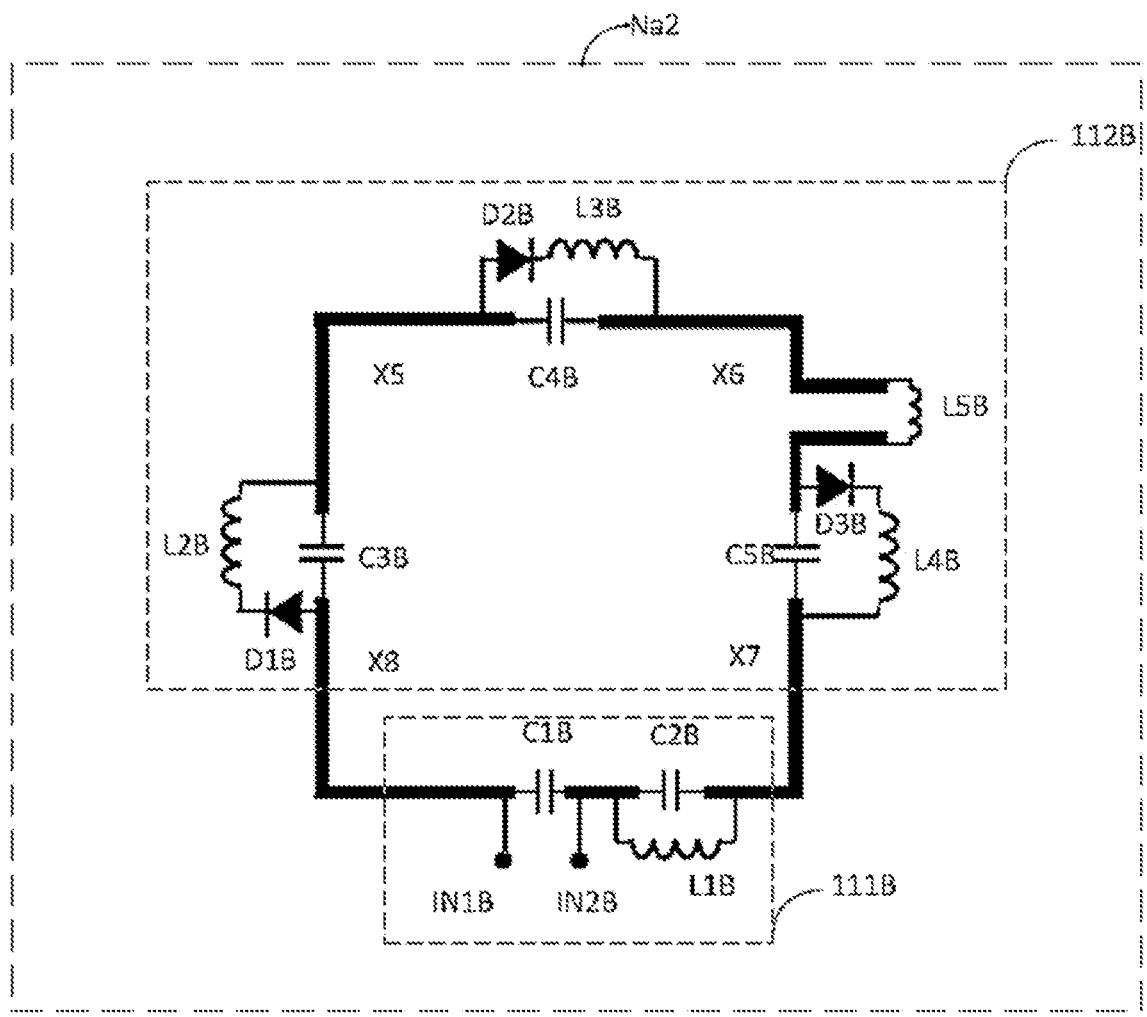
FIG. 5 is a circuit diagram of a coil Na2 according to embodiment one of the present application.

Referring to FIG. 5, FIG. 5 is a circuit diagram of the coil Na2. The wires X5, X6, X7, and X8 of the coil Na2 enclose a rectangle with a raised structure. The wire X5, the wire X7, and the wire X8 are L-shaped wires. The wire X6 includes a Z-shaped wire and an L-shaped wire. The raised structure is formed between the Z-shaped wire and the L-shaped wire to connect an inductor L5B. A secondary detuning circuit composed of an inductor L2B, a diode D1B, and a capacitor C3B is connected between the wire X5 and the wire X8. A secondary detuning circuit composed of an inductor L3B, a diode D2B, and a capacitor C4B is connected between the wire X5 and the wire X6. A secondary detuning circuit composed of an inductor L4B, a diode D3B, and a capacitor C5B is connected between the wire X6 and the wire X7. A first interface circuit 111B is connected between the wire X8 and the wire X7. The first interface circuit 111B includes an input end IN1B, an input end IN2B, a capacitor C1B, a capacitor C2B, and an inductor L1B. The input end IN1B is connected to a first end of the capacitor C1B. A second end of the capacitor C1B is connected to a first end of the capacitor C2B. A second end of the capacitor C2B is connected to a first end of the inductor L1B. A second end of the inductor L1B is connected to the first end of the capacitor C2B. The input end IN2B is connected to the second end of the capacitor C1B. The first detuning circuit 112B includes the inductor L2B, the inductor L3B, the inductor L4B, the inductor L5B, the capacitor C3B, the capacitor C4B, the capacitor C5B, the diode D1B, the diode D2B, and the diode D3B. A first end of the inductor L2B is connected to a first end of the capacitor C3B. A second end of the inductor L2B is connected to a negative electrode of the diode D1B. A positive electrode of the diode D1B is connected to a second end of the capacitor C3B. A second end of the capacitor C4B is connected to the first end of the capacitor C3B. A positive electrode of the diode D2B is connected to the second end of the capacitor C4B. A negative electrode of the diode D2B is connected to a second end of the inductor L3B. A first end of the inductor L3B is connected to a first end of the capacitor C4B. A positive electrode of the diode D3B is connected to a second end of the capacitor C5B. A negative electrode of the diode D3B is connected to a second end of the inductor L4B. A first end of the inductor L4B is connected to a first end of the capacitor C5B. A first end of the inductor L5B is connected to the second end of the capacitor C5B. A second end of the inductor L5B is connected to the first end of the capacitor C4B.

Figure 6:
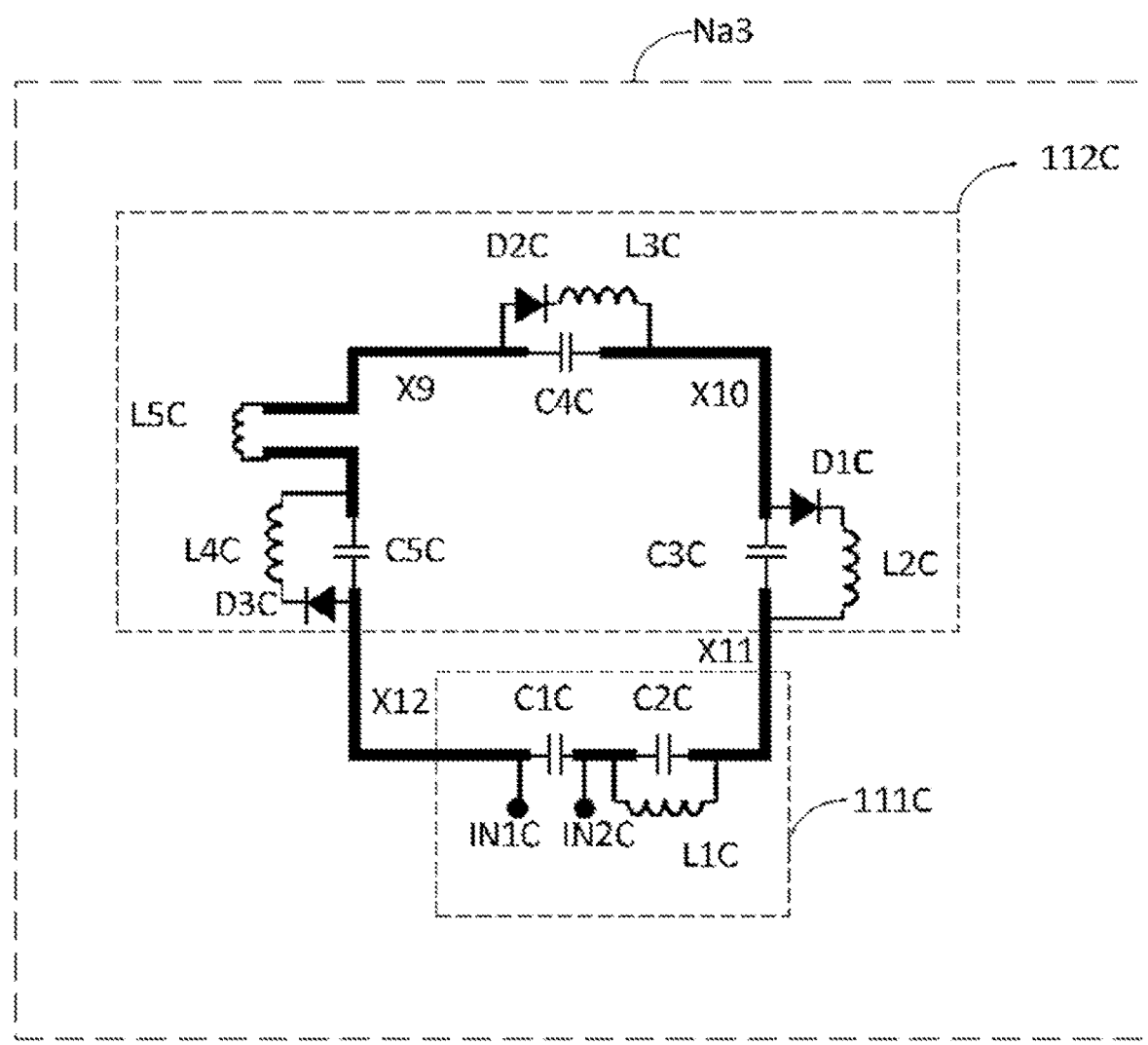
FIG. 6 is a circuit diagram of a coil Na3 according to embodiment one of the present application.

Referring to FIG. 6, FIG. 6 is a circuit diagram of the coil Na3. The wires X9, X10, X11, and X12 of the coil Na3 enclose a rectangle with a raised structure. The wire X10, the wire X11, and the wire X12 are L-shaped wires. The wire X9 includes a Z-shaped wire and an L-shaped wire. The raised structure is formed between the Z-shaped wire and the L-shaped wire to connect an inductor L5C. A secondary detuning circuit composed of an inductor L2C, a diode D1C, and a capacitor C3C is connected between the wire X10 and the wire X11. A secondary detuning circuit composed of an inductor L3C, a diode D2C, and a capacitor C4C is connected between the wire X9 and the wire X10. A secondary detuning circuit composed of an inductor L4C, a diode D3C, and a capacitor C5C is connected between the wire X9 and the wire X12. A first interface circuit 111C is connected between the wire X11 and the wire X12. In this embodiment, the inductor L5A of the coil Na1 and the inductor L5C of the coil Na3 are disposed adjacent to each other and corresponding to each other and are used for the decoupling between the coil Na1 and the coil Na3. Decoupling is implemented by adjusting the overlapping area of the inductor coils between the inductor L5A and the inductor L5C. The first interface circuit 111C includes an input end IN1C, an input end IN2C, a capacitor C1C, a capacitor C2C, and an inductor L1C. The input end IN1C is connected to a first end of the capacitor C1C. A second end of the capacitor C1C is connected to a first end of the capacitor C2C. A second end of the capacitor C2C is connected to a first end of the inductor L1C. A second end of the inductor L1C is connected to the first end of the capacitor C2C. The input end IN2C is connected to the second end of the capacitor C1C. The first detuning circuit 112C includes the inductor L2C, the inductor L3C, the inductor L4C, the inductor L5C, the capacitor C3C, the capacitor C4C, the capacitor C5C, the diode D1C, the diode D2C, and the diode D3C. A first end of the inductor L2C is connected to a first end of the capacitor C3C. A second end of the inductor L2C is connected to a negative electrode of the diode D1C. A positive electrode of the diode D1C is connected to a second end of the capacitor C3C. A second end of the capacitor C4C is connected to the second end of the capacitor C3C. A positive electrode of the diode D2C is connected to a first end of the capacitor C4C. A negative electrode of the diode D2C is connected to a second end of the inductor L3C. A first end of the inductor L3C is connected to the second end of the capacitor C4C. A positive electrode of the diode D3C is connected to a second end of the capacitor C5C. A negative electrode of the diode D3C is connected to a second end of the inductor L4C. A first end of the inductor L4C is connected to a first end of the capacitor C5C. A first end of the inductor L5C is connected to the first end of the capacitor C5C. A second end of the inductor L5C is connected to the first end of the capacitor C4C.

Figure 7:
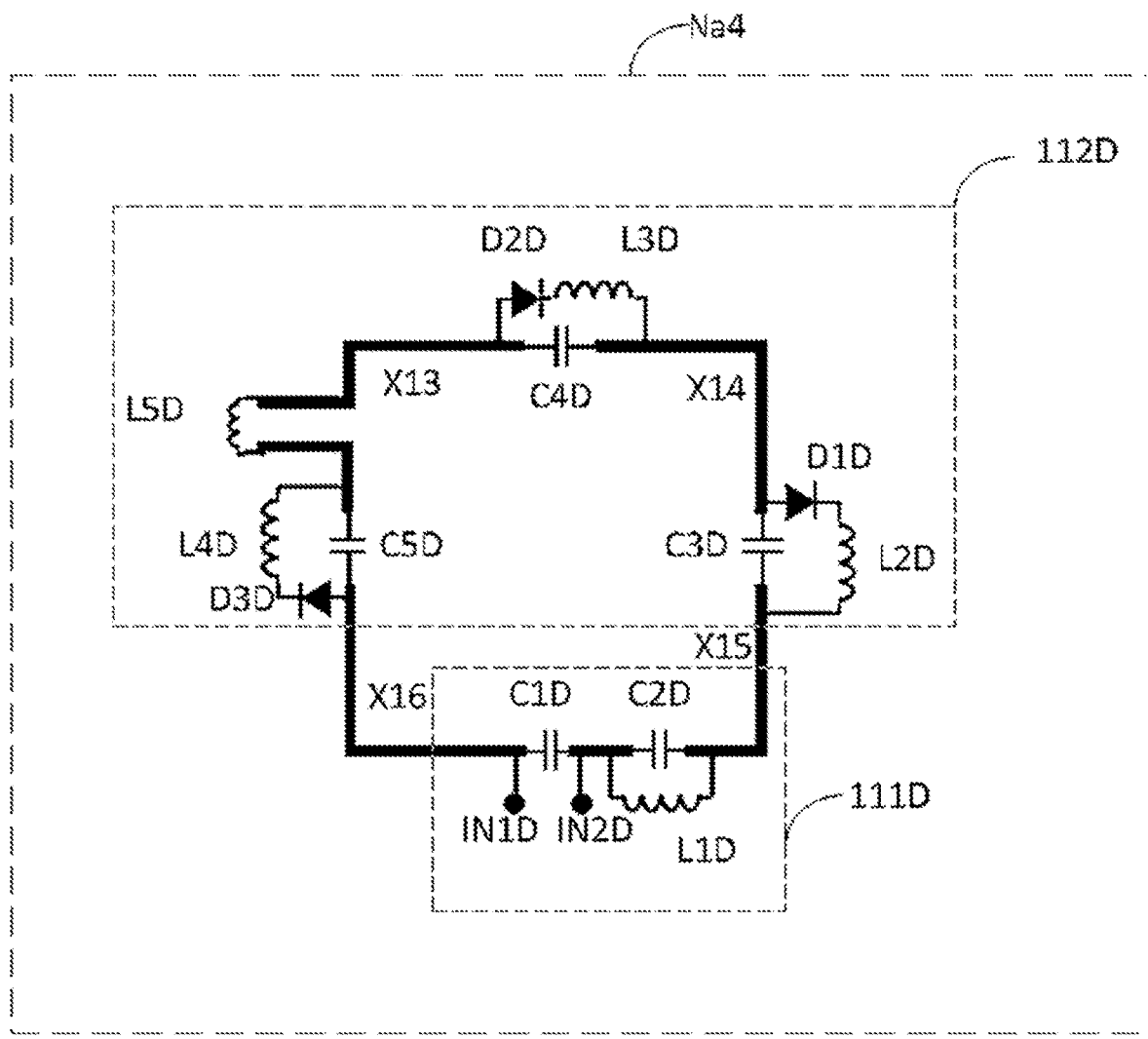
FIG. 7 is a circuit diagram of a coil Na4 according to embodiment one of the present application.

Referring to FIG. 7, FIG. 7 is a circuit diagram of the coil Na4. The wires X13, X14, X15, and X16 of the coil Na4 enclose a rectangle with a raised structure. The wire X14, the wire X15, and the wire X16 are L-shaped wires. The wire X13 includes a Z-shaped wire and an L-shaped wire. The raised structure is formed between the Z-shaped wire and the L-shaped wire to connect an inductor L5D. A secondary detuning circuit composed of an inductor L2D, a diode D1D, and a capacitor C3D is connected between the wire X14 and the wire X15. A secondary detuning circuit composed of an inductor L3D, a diode D2D, and a capacitor C4D is connected between the wire X13 and the wire X14. A secondary detuning circuit composed of an inductor L4D, a diode D3D, and a capacitor C5D is connected between the wire X13 and the wire X16. A first interface circuit 111D is connected between the wire X15 and the wire X16. In this embodiment, the inductor L5B of the coil Na2 and the inductor L5D of the coil Na4 are disposed adjacent to each other and corresponding to each other and are used for the decoupling between the coil Na2 and the coil Na4. Decoupling is implemented by adjusting the overlapping area of the inductor coils between the inductor L5B and the inductor L5D. The first interface circuit 111D includes an input end IN1D, an input end IN2D, a capacitor C1D, a capacitor C2D, and an inductor L1D. The input end IN1D is connected to a first end of the capacitor C1D. A second end of the capacitor C1D is connected to a first end of the capacitor C2D. A second end of the capacitor C2D is connected to a first end of the inductor L1D. A second end of the inductor L1D is connected to the first end of the capacitor C2D. The input end IN2D is connected to the second end of the capacitor C1D. The first detuning circuit 112D includes the inductor L2D, the inductor L3D, the inductor L4D, the inductor L5D, the capacitor C3D, the capacitor C4D, the capacitor C5D, the diode D1D, the diode D2D, and the diode D3D. A first end of the inductor L2D is connected to a first end of the capacitor C3D. A second end of the inductor L2D is connected to a negative electrode of the diode D1D. A positive electrode of the diode D1D is connected to a second end of the capacitor C3D. A second end of the capacitor C4D is connected to the second end of the capacitor C3D. A positive electrode of the diode D2D is connected to a first end of the capacitor C4D. A negative electrode of the diode D2D is connected to a second end of the inductor L3D. A first end of the inductor L3D is connected to the second end of the capacitor C4D. A positive electrode of the diode D3D is connected to a second end of the capacitor C5D. A negative electrode of the diode D3D is connected to a second end of the inductor L4D. A first end of the inductor L4D is connected to a first end of the capacitor C5D. A first end of the inductor L5D is connected to the first end of the capacitor C5D. A second end of the inductor L5D is connected to the first end of the capacitor C4D.

Figure 8:
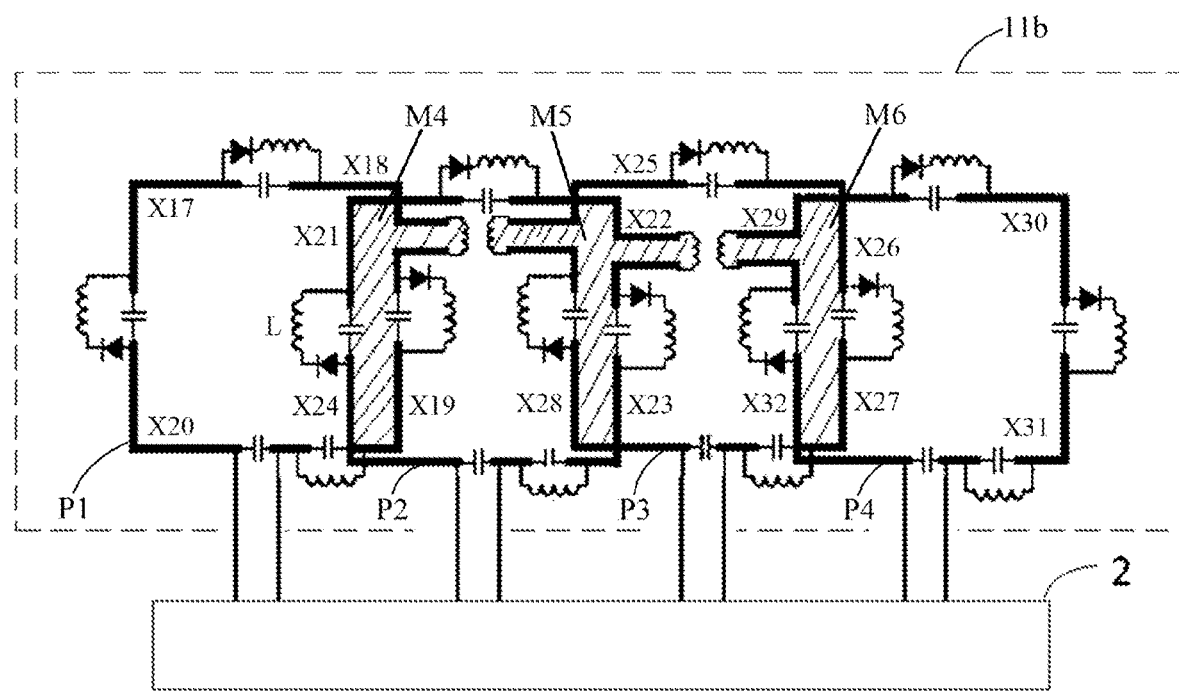
FIG. 8 is a circuit diagram of a second sub-coil array according to embodiment one of the present application.

Referring to FIG. 8, FIG. 8 is a circuit diagram of the second sub-coil array according to embodiment one of the present application. A second sub-coil array 11b includes multiple second coil units (a coil P1, a coil P2, a coil P3, and a coil P4). The multiple second coil units are superimposed based on a second preset phase difference. The coil P1, the coil P2, the coil P3, and the coil P4 are P coils. The wires X18 and X19 of the coil P1 and the wires X21 and X24 of the coil P2 enclose an overlapping region M4 with area A4. The wires X22 and X23 of the coil P2 and the wires X25 and X28 of the coil P3 enclose an overlapping region M5 with area A5. The wires X26 and X27 of the coil P3 and the wires X29 and X32 of the coil P4 enclose an overlapping region M6 with area A6. By superimposing the multiple second coil units in the second sub-coil array 11b, the effect of decoupling adjacent coil channels is implemented, and the interference between the P coils is reduced.

Figure 9:
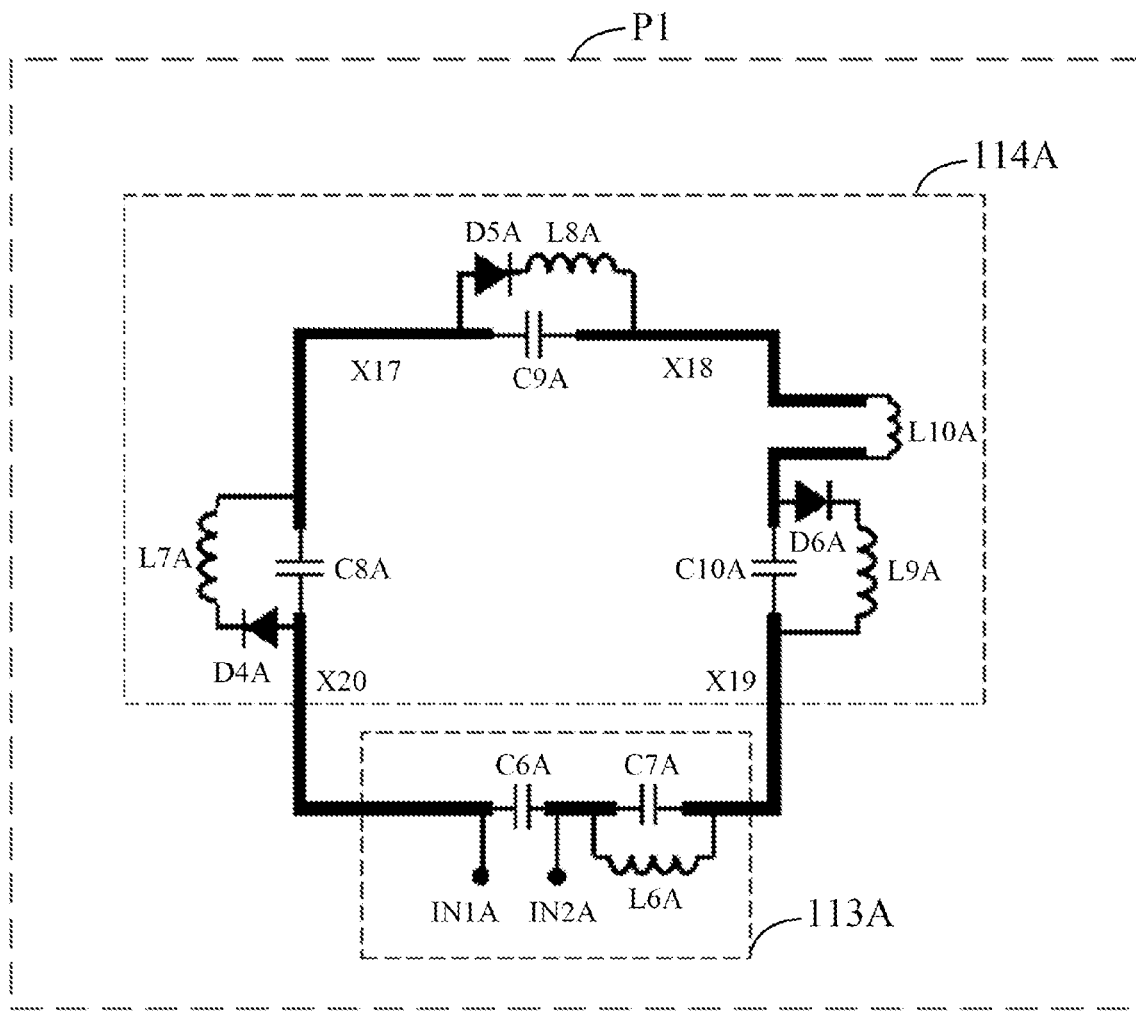
FIG. 9 is a circuit diagram of a coil P1 according to embodiment one of the present application.

Referring to FIG. 9, the coil P1 of the second coil units includes a second interface circuit 113A and a second detuning circuit 114A. The second detuning circuit 114A is connected to the second interface circuit 113A. The second interface circuit 113A is connected to the front-end module 2. The second interface circuit 113A includes an input end IN1A, an input end IN2A, a capacitor C6A, a capacitor C7A, and an inductor L6A. The input end IN1A is connected to a first end of the capacitor C6A. A second end of the capacitor C6A is connected to a first end of the capacitor C7A. A second end of the capacitor C7A is connected to a first end of the inductor L6A. A second end of the inductor L6A is connected to the first end of the capacitor C7A. The input end IN2A is connected to the second end of the capacitor C6A. The second detuning circuit 114A includes the inductor L7A, the inductor L8A, the inductor L9A, the inductor L10A, the capacitor C8A, the capacitor C9A, the capacitor C10A, the diode D4A, the diode D5A, and the diode D6A. A first end of the inductor L7A is connected to a first end of the capacitor C8A. A second end of the inductor L7A is connected to a negative electrode of the diode D4A. A positive electrode of the diode D4A is connected to a second end of the capacitor C8A. A second end of the capacitor C9A is connected to the first end of the capacitor C8A. A positive electrode of the diode D5A is connected to the second end of the capacitor C9A. A negative electrode of the diode D5A is connected to a second end of the inductor L8A. A first end of the inductor L8A is connected to a first end of the capacitor C9A. A positive electrode of the diode D6A is connected to a second end of the capacitor C10A. A negative electrode of the diode D6A is connected to a second end of the inductor L9A. A first end of the inductor L9A is connected to a first end of the capacitor C10A. A first end of the inductor L10A is connected to the second end of the capacitor C10A. A second end of the inductor L10A is connected to the first end of the capacitor C9A.

Figure 10:
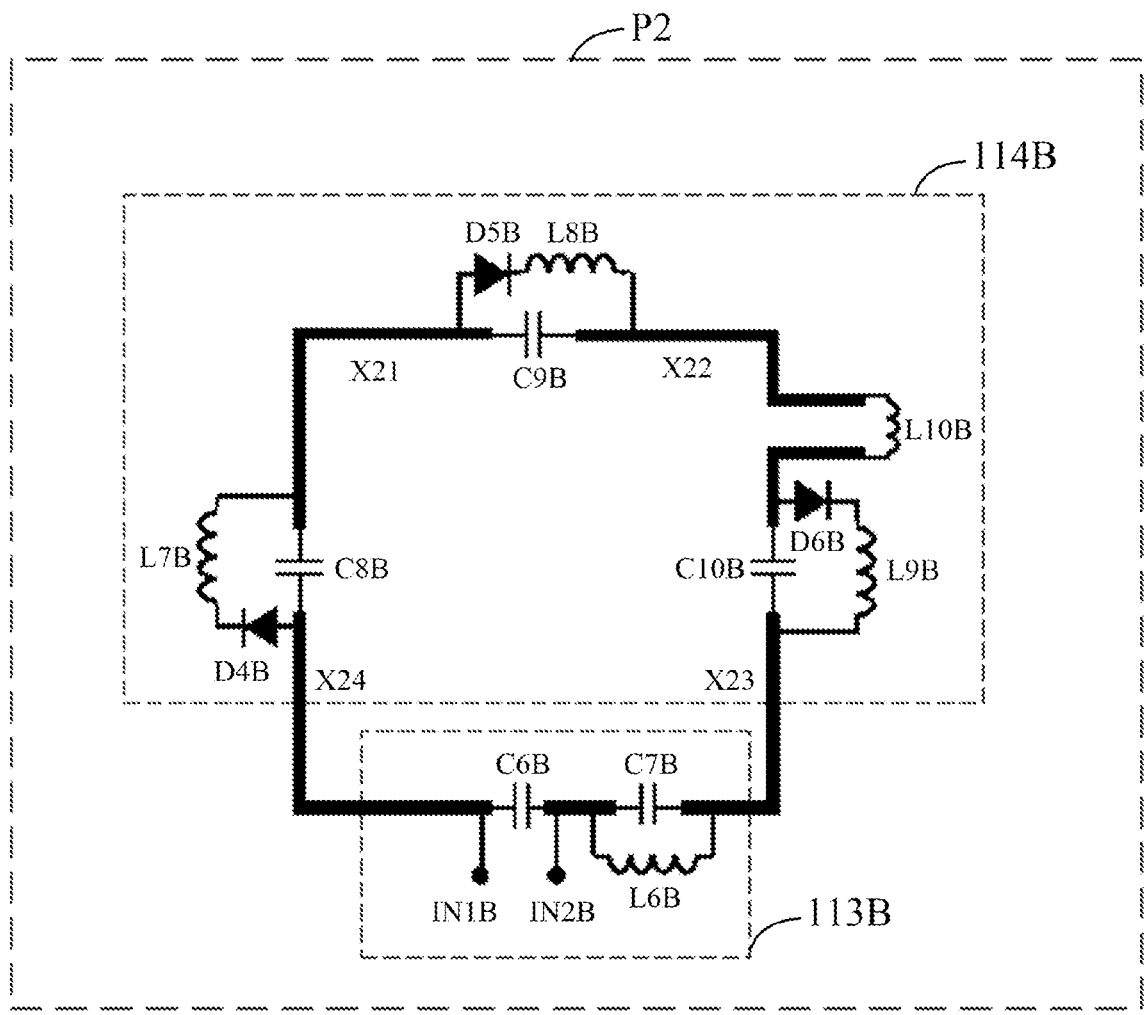
FIG. 10 is a circuit diagram of a coil P2 according to embodiment one of the present application.

Referring to FIG. 10, the coil P2 of the second coil units includes a second interface circuit 113B and a second detuning circuit 114B. The second detuning circuit 114B is connected to the second interface circuit 113B. The second interface circuit 113B is connected to the front-end module 2. The second interface circuit 113B includes an input end IN1B, an input end IN2B, a capacitor C6B, a capacitor C7B, and an inductor L6B. The input end IN1B is connected to a first end of the capacitor C6B. A second end of the capacitor C6B is connected to a first end of the capacitor C7B. A second end of the capacitor C7B is connected to a first end of the inductor L6B. A second end of the inductor L6B is connected to the first end of the capacitor C7B. The input end IN2B is connected to the second end of the capacitor C6B. The second detuning circuit 114B includes an inductor L7B, an inductor L8B, an inductor L9B, an inductor L10B, a capacitor C8B, a capacitor C9B, a capacitor C10B, a diode D4B, a diode D5B, and a diode D6B. A first end of the inductor L7B is connected to a first end of the capacitor C8B. A second end of the inductor L7B is connected to a negative electrode of the diode D4B. A positive electrode of the diode D4B is connected to a second end of the capacitor C8B. A second end of the capacitor C9B is connected to the second end of the capacitor C8B. A positive electrode of the diode D5B is connected to a first end of the capacitor C9B. A negative electrode of the diode D5B is connected to a second end of the inductor L8B. A first end of the inductor L8B is connected to the second end of the capacitor C9B. A positive electrode of the diode D6B is connected to a second end of the capacitor C10B. A negative electrode of the diode D6B is connected to a second end of the inductor L9B. A first end of the inductor L9B is connected to a first end of the capacitor C10B. A first end of the inductor L10B is connected to the first end of the capacitor C10B. A second end of the inductor L10B is connected to the first end of the capacitor C9B.

Figure 11:
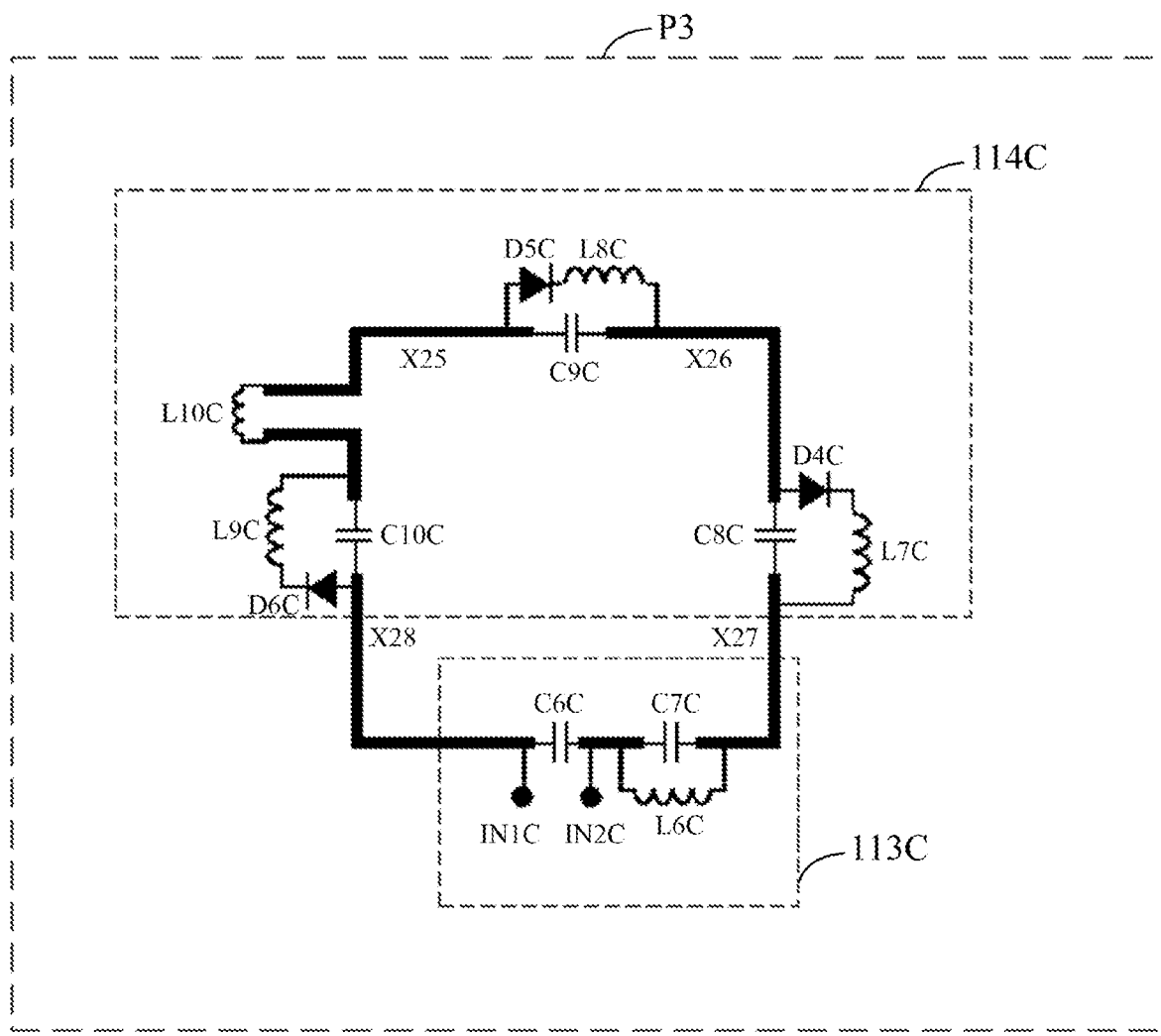
FIG. 11 is a circuit diagram of a coil P3 according to embodiment one of the present application.

Referring to FIG. 11, the coil P3 of the second coil units includes a second interface circuit 113C and a second detuning circuit 114C. The second detuning circuit 114C is connected to the second interface circuit 113C. The second interface circuit 113C is connected to the front-end module 2. The second interface circuit 113C includes an input end IN1C, an input end IN2C, a capacitor C6C, a capacitor C7C, and an inductor L6C. The input end IN1C is connected to a first end of the capacitor C6C. A second end of the capacitor C6C is connected to a first end of the capacitor C7C.

A second end of the capacitor C7C is connected to a first end of the inductor L6C. A second end of the inductor L6C is connected to the first end of the capacitor C7C. The input end IN2C is connected to the second end of the capacitor C6C. The second detuning circuit 114C includes an inductor L7C, an inductor L8C, an inductor L9C, an inductor L10C, a capacitor C8C, a capacitor C9C, a capacitor C10C, a diode D4C, a diode D5C, and a diode D6C. A first end of the inductor L7C is connected to a first end of the capacitor C8C. A second end of the inductor L7C is connected to a negative electrode of the diode D4C. A positive electrode of the diode D4C is connected to a second end of the capacitor C8C. A second end of the capacitor C9C is connected to the second end of the capacitor C8C. A positive electrode of the diode D5C is connected to a first end of the capacitor C9C. A negative electrode of the diode D5C is connected to a second end of the inductor L8C. A first end of the inductor L8C is connected to the second end of the capacitor C9C. A positive electrode of the diode D6C is connected to a second end of the capacitor C10C. A negative electrode of the diode D6C is connected to a second end of the inductor L9C. A first end of the inductor L9C is connected to a first end of the capacitor C10C. A first end of the inductor L10C is connected to the first end of the capacitor C10C. A second end of the inductor L10C is connected to the first end of the capacitor C9C.

Figure 12:
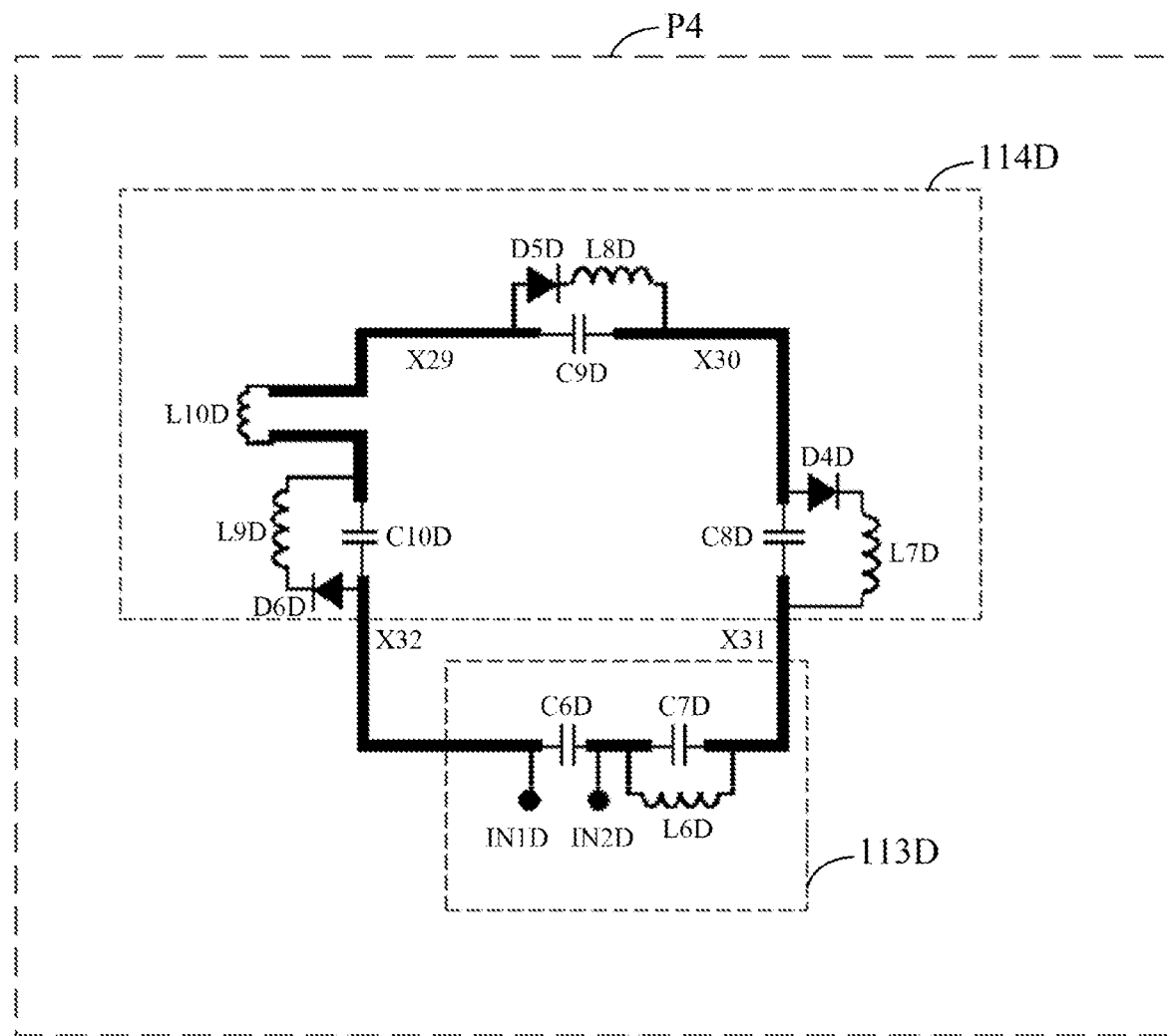
FIG. 12 is a circuit diagram of a coil P4 according to embodiment one of the present application.

Referring to FIG. 12, the coil P4 of the second coil units includes a second interface circuit 113D and a second detuning circuit 114D. The second detuning circuit 114D is connected to the second interface circuit 113D. The second interface circuit 113D is connected to the front-end module 2. The second interface circuit 113D includes an input end IN1D, an input end IN2D, a capacitor C6D, a capacitor C7D, and an inductor L6D. The input end IN1D is connected to a first end of the capacitor C6D. A second end of the capacitor C6D is connected to a first end of the capacitor C7D. A second end of the capacitor C7D is connected to a first end of the inductor L6D. A second end of the inductor L6D is connected to the first end of the capacitor C7D. The input end IN2D is connected to the second end of the capacitor C6D. The second detuning circuit 114D includes an inductor L7D, an inductor L8D, an inductor L9D, an inductor L10D, a capacitor C8D, a capacitor C9D, a capacitor C10D, a diode D4D, a diode D5D, and a diode D6D. A first end of the inductor L7D is connected to a first end of the capacitor C8D. A second end of the inductor L7D is connected to a negative electrode of the diode D4D. A positive electrode of the diode D4D is connected to a second end of the capacitor C8D. A second end of the capacitor C9D is connected to the second end of the capacitor C8D. A positive electrode of the diode D5D is connected to a first end of the capacitor C9D. A negative electrode of the diode D5D is connected to a second end of the inductor L8D. A first end of the inductor L8D is connected to the second end of the capacitor C9D. A positive electrode of the diode D6D is connected to a second end of the capacitor C10D. A negative electrode of the diode D6D is connected to the second end of the inductor L9D. A first end of the inductor L9D is connected to a first end of the capacitor C10D. A first end of the inductor L10D is connected to the first end of the capacitor C10D. A second end of the inductor L10D is connected to the first end of the capacitor C9D.

The structures and principles of a first sub-coil unit 11a and a second sub-coil unit 11b are similar, and details are not described herein.

Figure 13:
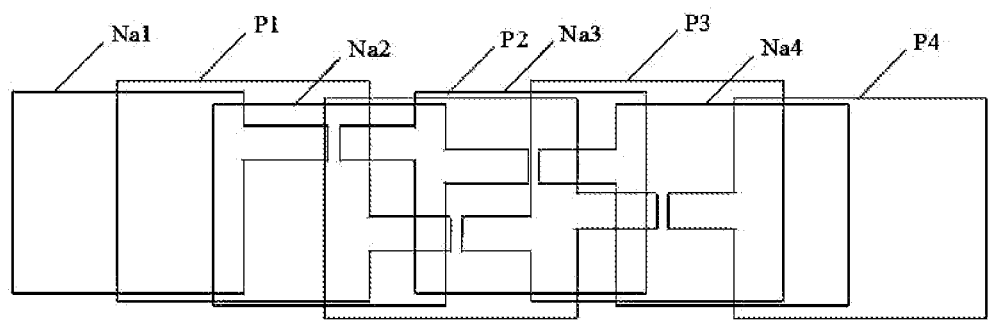
FIG. 13 is a diagram illustrating an arrangement of a first coil array according to embodiment one of the present application.

In this embodiment, the first coil array 11 includes four Na coils and four P coils. Referring to FIG. 13, FIG. 13 is a diagram illustrating an arrangement of the first coil array 11 according to embodiment one of the present application. The non-adjacent coils between the four Na coils (the coil Na1, the coil Na2, the coil Na3, and the coil Na4) are decoupled through inductors of raised portions of rectangles. The non-adjacent coils between the four P coils (the coil P1, the coil P2, the coil P3, and the coil P4) are also decoupled through inductors of raised portions of rectangles. The adjacent coils such as the coil Na1 and the coil Na2 are decoupled through the overlapping area.

In this embodiment, a nuclear magnetic test signal is input to the first interface circuit 111 through the input end IN1 of the first interface circuit 111 and the input end IN2 of the first interface circuit 111. The working states of the Na coils are controlled through the first detuning circuit 112 to allow Na imaging to be performed. A nuclear magnetic test signal is input to the second interface circuit 113 through the input end IN1 of the second interface circuit 113 and the input end IN2 of the second interface circuit 113. The working states of the P coils are controlled through the second detuning circuit 114 to allow P imaging to be performed. In this embodiment, the values of elements in each coil can be adjusted according to actual conditions and are not limited in this embodiment.

Figure 14:
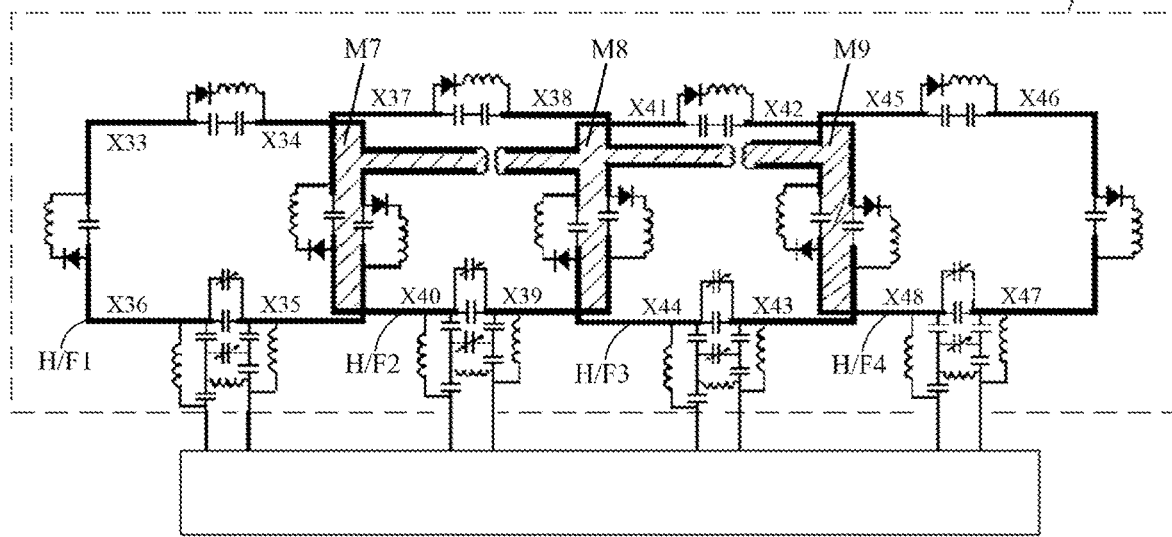
FIG. 14 is a circuit diagram of a second coil array according to embodiment one of the present application.

Referring to FIG. 14, FIG. 14 is a circuit diagram of the second coil array 12. In this embodiment, the H/F coils can transmit the radio frequency signals of the nuclide H and the nuclide F. In this embodiment, four H/F coils are described as an example. The second coil array 12 includes multiple third coil units (a coil H/F1, a coil H/F2, a coil H/F3, and a coil H/F4). The multiple third coil units are superimposed based on a third preset phase difference. The coil H/F1, the coil H/F2, the coil H/F3, and the coil H/F4 are H/F coils. The wires X34 and X35 of the coil H/F1 and the wires X37 and X40 of the coil H/F2 enclose an overlapping region M7 with area A7. The wires X38 and X39 of the coil H/F2 and the wires X41 and X44 of the coil H/F3 enclose an overlapping region M8 with area A8. The wires X42 and X43 of the coil H/F3 and the wires X45 and X48 of the coil H/F4 enclose an overlapping region M9 with area A9. By superimposing the multiple third coil units in the second coil array 12, the effect of decoupling adjacent coil channels is implemented.

Figure 15:
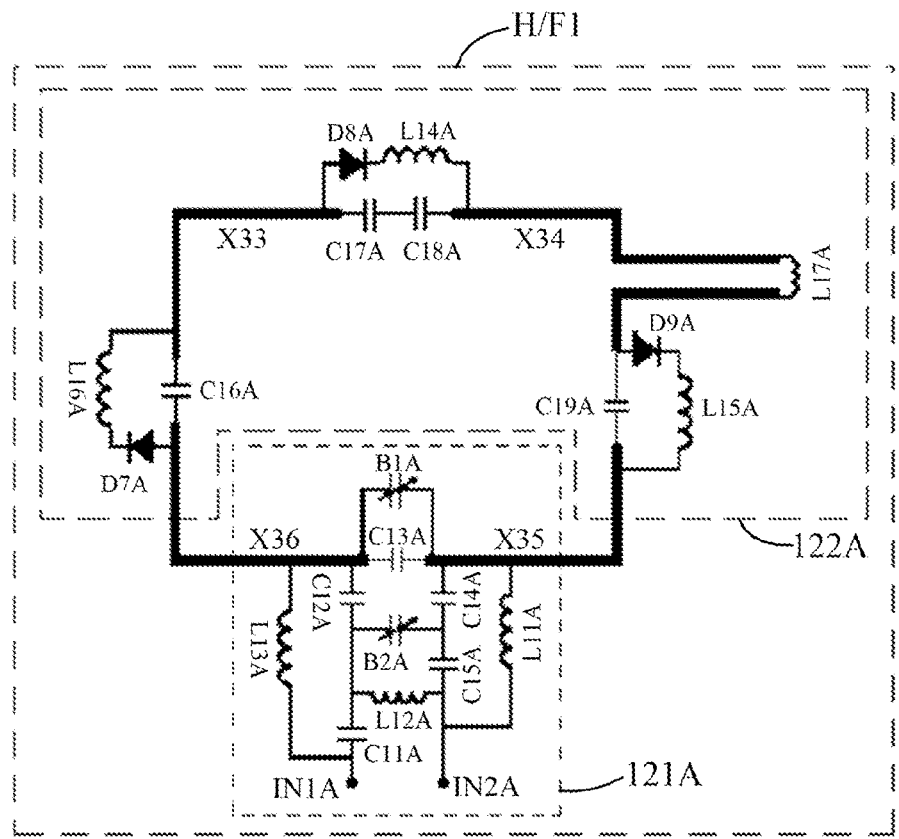
FIG. 15 is a circuit diagram of a coil H/F1 according to embodiment one of the present application.

The coil H/F1 in the third coil units includes a third interface circuit 121A and a third detuning circuit 122A. The third detuning circuit 122A is connected to the third interface circuit 121A. The third interface circuit 121A is connected to the front-end module 2. Referring to FIG. 15, FIG. 15 is a circuit diagram of the coil H/F1 in this embodiment. The wires X33, X34, X35, and X36 of the coil H/F1 enclose a rectangle with a raised structure. The wire X33, the wire X35, and the wire X36 are L-shaped wires. The wire X34 includes a Z-shaped wire and an L-shaped wire. The raised structure is formed between the Z-shaped wire and the L-shaped wire to connect an inductor L17A. A secondary detuning circuit composed of an inductor L16A, a diode D7A, and a capacitor C16A is connected between the wire X33 and the wire X36. A secondary detuning circuit composed of an inductor L14A, a diode D8A, a capacitor C17A, and a capacitor C18A is connected between the wire X33 and the wire X34. A secondary detuning circuit composed of an inductor L15A, a diode D9A, and a capacitor C19A is connected between the wire X34 and the wire X35. The third interface circuit 121A is connected between the wire X36 and the wire X35. The third interface circuit 121A includes an input end IN1A, an input end IN2A, a capacitor C11A, a capacitor C12A, a capacitor C13A, a capacitor C14A, a capacitor C15A, a variable capacitor B1A, a variable capacitor B2A, an inductor L11A, an inductor L12A, and an inductor L13A. The input end IN1A is connected to a first end of the capacitor C11A. A second end of the capacitor C11A is connected to a first end of the capacitor C12A. A first end of the inductor L13A is connected to a second end of the capacitor C12A. A second end of the inductor L13A is connected to the first end of the capacitor C11A. A first end of the capacitor C13A is connected to the second end of the capacitor C12A. A second end of the capacitor C13A is connected to a first end of the capacitor C14A. A second end of the capacitor C14A is connected to a first end of the capacitor C15A. A second end of the capacitor C15A is connected to the input end IN2A. A first end of the inductor L12A is connected to the second end of the capacitor C11A. A second end of the inductor L12A is connected to the second end of the capacitor C15A. A first end of the inductor L11A is connected to the first end of the capacitor C14A. A second end of the inductor L11A is connected to the second end of the capacitor C15A. A first end of the variable capacitor B1A is connected to a first end of the capacitor C13A. A second end of the variable capacitor B1A is connected to a second end of the capacitor C13A. A first end of the variable capacitor B2A is connected to the first end of the capacitor C12A. A second end of the variable capacitor B2A is connected to the second end of the capacitor C15A. The third detuning circuit 122A includes a capacitor C16A, a capacitor C17A, a capacitor C18A, a capacitor C19A, an inductor L14A, an inductor L15A, an inductor L16A, an inductor L17A, a diode D7A, a diode D8A, and a diode D9A. A first end of the inductor L16A is connected to a first end of the capacitor C17A. A second end of the inductor L16A is connected to a negative electrode of the diode D7A. A positive electrode of the diode DA is connected to a second end of the capacitor C16A. A second end of the capacitor C17A is connected to a first end of the capacitor C16A. The first end of the capacitor C17A is connected to a second end of the capacitor C18A. A positive electrode of the diode D8A is connected to the second end of the capacitor C17A. A negative electrode of the diode D8A is connected to a second end of the inductor L14A. A first end of the inductor L14A is connected to a first end of the capacitor C18A. A positive electrode of the diode D9A is connected to a second end of the capacitor C19A. A negative electrode of the diode D9A is connected to a second end of the inductor L15A. A first end of the inductor L15A is connected to a first end of the capacitor C19A. A first end of the inductor L17A is connected to the first end of the capacitor C18A. A second end of the inductor L17A is connected to the second end of the capacitor C19A.

Figure 16:
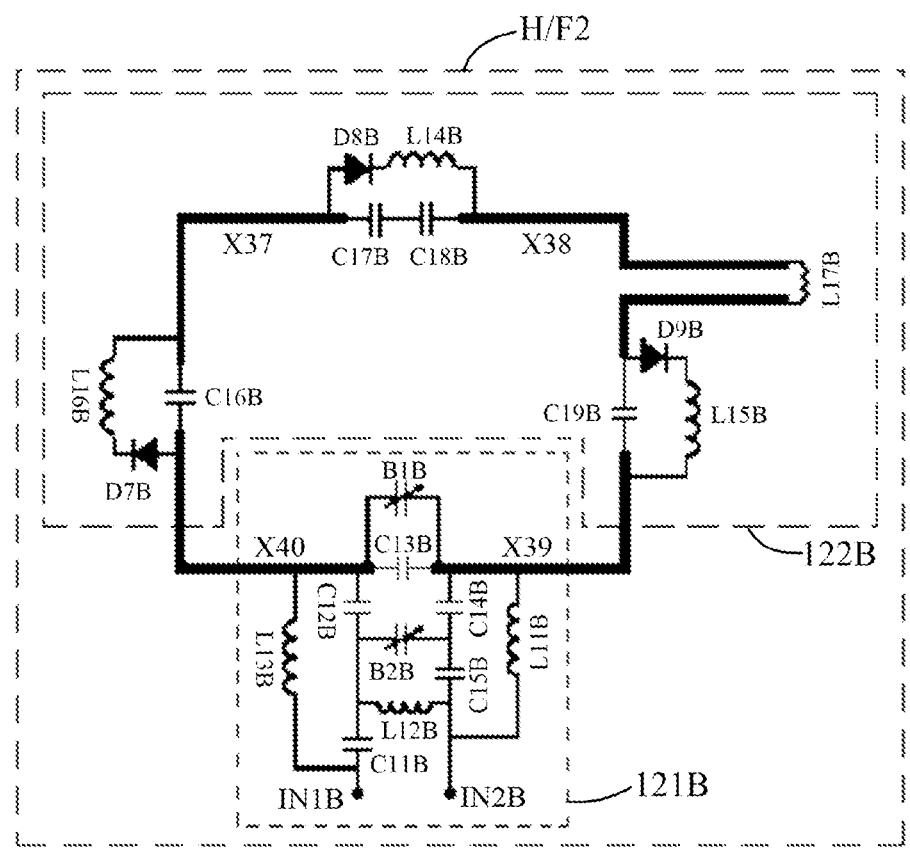
FIG. 16 is a circuit diagram of a coil H/F2 according to embodiment one of the present application.

Referring to FIG. 16, FIG. 16 is a circuit diagram of the coil H/F2 in this embodiment. The wires X37, X38, X39, and X40 of the coil H/F2 enclose a rectangle with a raised structure. The wire X37, the wire X39, and the wire X40 are L-shaped wires. The wire X38 includes a Z-shaped wire and an L-shaped wire. The raised structure is formed between the Z-shaped wire and the L-shaped wire to connect an inductor L17B. A secondary detuning circuit composed of an inductor L16B, a diode D7B, and a capacitor C16B is connected between the wire X37 and the wire X40. A secondary detuning circuit composed of an inductor L14B, a diode D8B, a capacitor C17B, and a capacitor C18B is connected between the wire X37 and the wire X38. A secondary detuning circuit composed of an inductor L15B, a diode D9B, and a capacitor C19B is connected between the wire X38 and the wire X39. A third interface circuit 121B is connected between the wire X39 and the wire X40. The third interface circuit 121B includes an input end IN1B, an input end IN2B, a capacitor C11B, a capacitor C12B, a capacitor C13B, a capacitor C14B, a capacitor C15B, a variable capacitor B1B, a variable capacitor B2B, an inductor L11B, an inductor L12B, and an inductor L13B. The input end IN1B is connected to a first end of the capacitor C11B. A second end of the capacitor C11B is connected to a first end of the capacitor C12B. A first end of the inductor L13B is connected to a second end of the capacitor C12B. A second end of the inductor L13B is connected to the first end of the capacitor C12B. A first end of the capacitor C13B is connected to the second end of the capacitor C12B. A second end of the capacitor C13B is connected to a first end of the capacitor C14B. A second end of the capacitor C14B is connected to a first end of the capacitor C15B. A second end of the capacitor C15B is connected to the input end IN2B. A first end of the inductor L12B is connected to the second end of the capacitor C11B. A second end of the inductor L12B is connected to the second end of the capacitor C15B. A first end of the inductor L11B is connected to the first end of the capacitor C14B. A second end of the inductor L11B is connected to the second end of the capacitor C15B. A first end of the variable capacitor B1B is connected to the first end of the capacitor C13B. A second end of the variable capacitor B1B is connected to the second end of the capacitor C13B. A first end of the variable capacitor B2B is connected to the first end of the capacitor C12B. A second end of the variable capacitor B2B is connected to the second end of the capacitor C15B. A third detuning circuit 122B includes a capacitor C16B, a capacitor C17B, a capacitor C18B, a capacitor C19B, an inductor L14B, an inductor L15B, an inductor L16B, an inductor L17B, a diode D7B, a diode D8B, and a diode D9B. A first end of the inductor L16B is connected to a first end of the capacitor C16B. A second end of the inductor L16B is connected to a negative electrode of the diode D7B. A positive electrode of the diode D7B is connected to a second end of the capacitor C16B. A second end of the capacitor C17B is connected to the first end of the capacitor C16B. A first end of the capacitor C17B is connected to a second end of the capacitor C18B. A positive electrode of the diode D8B is connected to the second end of the capacitor C17B. A negative electrode of the diode D8B is connected to a second end of the inductor L14B. A first end of the inductor L14B is connected to a first end of the capacitor C18B. A positive electrode of the diode D9B is connected to a second end of the capacitor C19B. A negative electrode of the diode D11B is connected to a second end of the inductor L15B. A first end of the inductor L15B is connected to a first end of the capacitor C19B. A first end of the inductor L17B is connected to the first end of the capacitor C18B. A second end of the inductor L17B is connected to the second end of the capacitor C19B.

Figure 17:
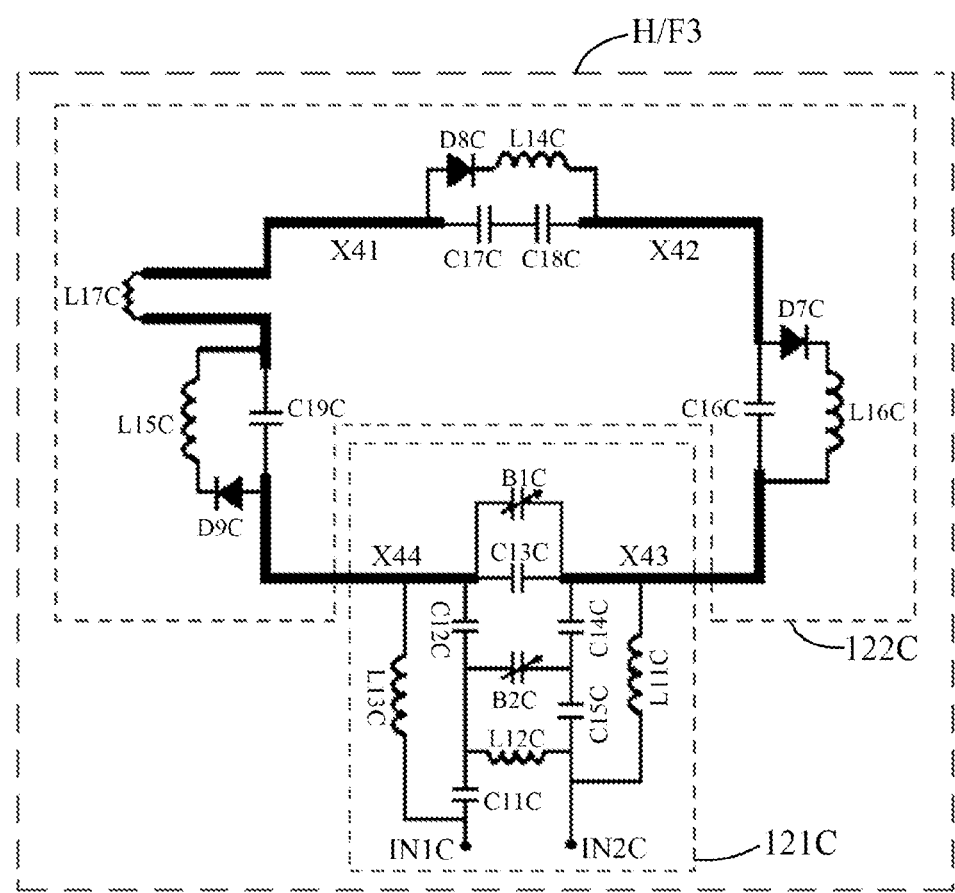
FIG. 17 is a circuit diagram of a coil H/F3 according to embodiment one of the present application.

Referring to FIG. 17, FIG. 17 is a circuit diagram of the coil H/F3 in this embodiment. The wires X41, X42, X43, and X44 of the coil H/F3 enclose a rectangle with a raised structure. The wire X42, the wire X43, and the wire X44 are L-shaped wires. The wire X41 includes a Z-shaped wire and an L-shaped wire. The raised structure is formed between the Z-shaped wire and the L-shaped wire to connect an inductor L17C. A secondary detuning circuit composed of an inductor L16C, a diode D7C, and a capacitor C16C is connected between the wire X42 and the wire X43. A secondary detuning circuit composed of an inductor L14C, a diode D8C, a capacitor C17C, and a capacitor C18C is connected between the wire X41 and the wire X42. A secondary detuning circuit composed of an inductor L15C, a diode D11C, and a capacitor C19C is connected between the wire X41 and the wire X44. A second interface circuit 121C is connected between the wire X43 and the wire X44. In this embodiment, the inductor L17A of the coil H/F1 and the inductor L17C of the coil H/F3 are disposed adjacent to each other and corresponding to each other and are used for the decoupling between the coil H/F1 and the coil H/F3. Decoupling is implemented by adjusting the overlapping area of the inductor coils between the inductor L17A and the inductor L17C. A third interface circuit 121C includes an input end IN1C, an input end IN2C, a capacitor C11C, a capacitor C12C, a capacitor C13C, a capacitor C14C, a capacitor C15C, a variable capacitor B1C, a variable capacitor B2C, an inductor L11C, an inductor L12C, and an inductor L13C. The input end IN1C is connected to a first end of the capacitor C11C. A second end of the capacitor C11C is connected to a first end of the capacitor C12C. A first end of the inductor L13C is connected to a second end of the capacitor C12C. A second end of the inductor L13C is connected to the first end of the capacitor C11C. A first end of the capacitor C13C is connected to the second end of the capacitor C12C. A second end of the capacitor C13C is connected to a first end of the capacitor C14C. A second end of the capacitor C14C is connected to a first end of the capacitor C15C. A second end of the capacitor C15C is connected to the input end IN2C. A first end of the inductor L12C is connected to the second end of the capacitor C11C. A second end of the inductor L12C is connected to the second end of the capacitor C15C. A first end of the inductor L11C is connected to the first end of the capacitor C14C. A second end of the inductor L11C is connected to the second end of the capacitor C15C. A first end of the variable capacitor B1C is connected to the first end of the capacitor C13C. A second end of the variable capacitor B1C is connected to the second end of the capacitor C13C. A first end of the variable capacitor B2C is connected to the first end of the capacitor C12C. A second end of the variable capacitor B2C is connected to the second end of the capacitor C15C. A third detuning circuit 122C includes a capacitor C16C, a capacitor C17C, a capacitor C18C, a capacitor C19C, an inductor L14C, an inductor L15C, an inductor L16C, an inductor L17C, a diode D7C, a diode D8C, and a diode D9C. A first end of the inductor L16C is connected to a first end of the capacitor C16C. A second end of the inductor L16C is connected to a negative electrode of the diode D7C. A positive electrode of the diode D7C is connected to a second end of the capacitor C16C. A second end of the capacitor C18C is connected to the second end of the capacitor C16C. A first end of the capacitor C17C is connected to a first end of the capacitor C18C. A positive electrode of the diode D8C is connected to a second end of the capacitor C17C. A negative electrode of the diode D8C is connected to a second end of the inductor L14C. A first end of the inductor L14C is connected to the second end of the capacitor C18C. A positive electrode of the diode D9C is connected to a second end of the capacitor C19C. A negative electrode of the diode D9C is connected to a second end of the inductor L15C. A first end of the inductor L15C is connected to a first end of the capacitor C19C. A first end of the inductor L17C is connected to the second end of the capacitor C17C. A second end of the inductor L17C is connected to the first end of the capacitor C19C.

Figure 18:
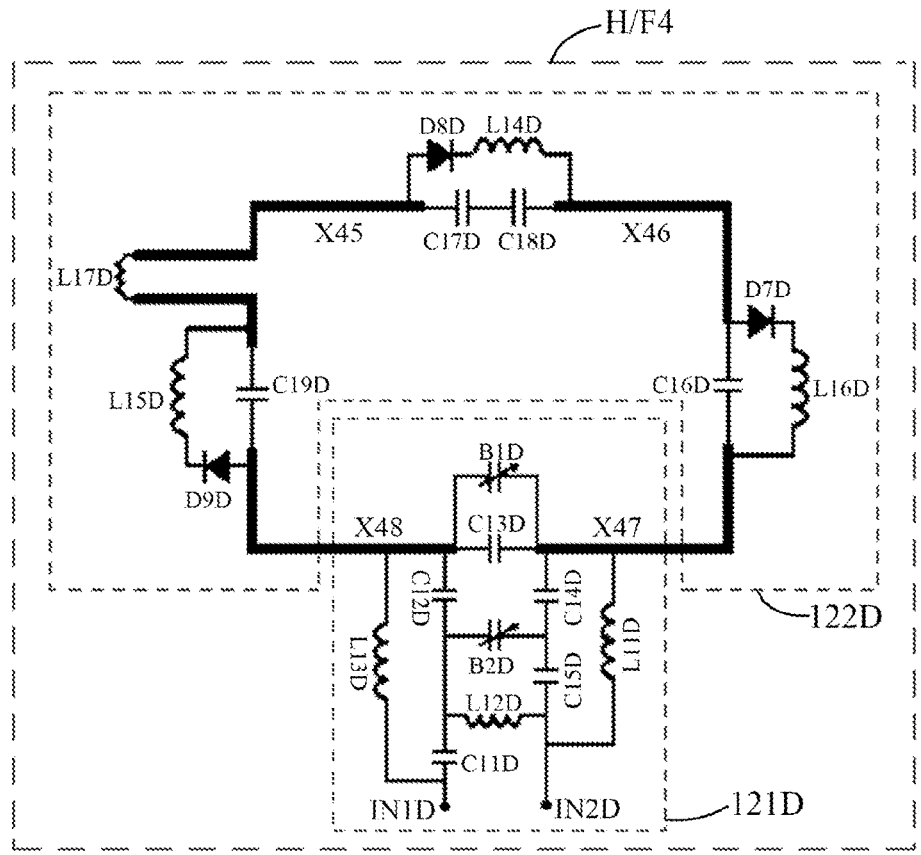
FIG. 18 is a circuit diagram of a coil H/F4 according to embodiment one of the present application.

Referring to FIG. 18, FIG. 18 is a circuit diagram of the coil H/F4 in this embodiment. The wires X45, X46, X47, and X48 of the coil H/F4 enclose a rectangle with a raised structure. The wire X46, the wire X47, and the wire X48 are L-shaped wires. The wire X45 includes a Z-shaped wire and an L-shaped wire. The raised structure is formed between the Z-shaped wire and the L-shaped wire to connect an inductor L17D. A secondary detuning circuit composed of an inductor L16D, a diode D7D, and a capacitor C16D is connected between the wire X46 and the wire X47. A secondary detuning circuit composed of an inductor L14D, a diode D8D, a capacitor C17D, and a capacitor C18D is connected between the wire X45 and the wire X46. A secondary detuning circuit composed of an inductor L15D, a diode D9D, and a capacitor C19D is connected between the wire X45 and the wire X48. A second interface circuit 121D is connected between the wire X47 and the wire X48. In this embodiment, the inductor L17B of the coil H/F2 and the inductor L17D of the coil H/F4 are disposed adjacent to each other and corresponding to each other and are used for the decoupling between the coil H/F2 and the coil H/F4. Decoupling is implemented by adjusting the overlapping area of the inductor coils between the inductor L17B and the inductor L17D. The third interface circuit 121D includes an input end IN1D, an input end IN2D, a capacitor C11D, a capacitor C12D, a capacitor C13D, a capacitor C14D, a capacitor C15D, a variable capacitor B1D, a variable capacitor B2D, an inductor L11D, an inductor L12D, and an inductor L13D. The input end IN1D is connected to a first end of the capacitor C11D. A second end of the capacitor C11D is connected to a first end of the capacitor C12D. A first end of the inductor L13D is connected to a second end of the capacitor C12D. A second end of the inductor L13D is connected to the first end of the capacitor C11D. A first end of the capacitor C13D is connected to the second end of the capacitor C12D. A second end of the capacitor C13D is connected to a first end of the capacitor C14D. A second end of the capacitor C14D is connected to a first end of the capacitor C15D. A second end of the capacitor C15D is connected to the input end IN2D. A first end of the inductor L12D is connected to the second end of the capacitor C11D. A second end of the inductor L12D is connected to the second end of the capacitor C15D. A first end of the inductor L11D is connected to the first end of the capacitor C14D. A second end of the inductor L11D is connected to the second end of the capacitor C15D. A first end of the variable capacitor B1D is connected to the first end of the capacitor C13D. A second end of the variable capacitor B1D is connected to the second end of the capacitor C13D. A first end of the variable capacitor B2D is connected to the first end of the capacitor C12D. A second end of the variable capacitor B2D is connected to the second end of the capacitor C15D. A third detuning circuit 122D includes a capacitor C16D, a capacitor C17D, a capacitor C18D, a capacitor C19D, an inductor L14D, an inductor L15D, an inductor L16D, an inductor L17D, a diode D7D, a diode D8D, and a diode D9D. A first end of the inductor L16D is connected to a first end of the capacitor C16D. A second end of the inductor L16D is connected to a negative electrode of the diode D7D. A positive electrode of the diode D7D is connected to a second end of the capacitor C16D. A second end of the capacitor C18D is connected to the second end of the capacitor C16D. A first end of the capacitor C17D is connected to a first end of the capacitor C18D. A positive electrode of the diode D8D is connected to a second end of the capacitor C17D. A negative electrode of the diode D8D is connected to a second end of the inductor L14D. A first end of the inductor L14D is connected to the second end of the capacitor C18D. A positive electrode of the diode D9D is connected to a second end of the capacitor C19D. A negative electrode of the diode D9D is connected to a second end of the inductor L15D. A first end of the inductor L15D is connected to a first end of the capacitor C19D. A first end of the inductor L17D is connected to the second end of the capacitor C17D. A second end of the inductor L17D is connected to the first end of the capacitor C19D.

In this embodiment, a nuclear magnetic test signal is input to the third interface circuit 121 through the input terminal IN1 of the third interface circuit 121 and the input terminal IN2 of the third interface circuit 121. The working states of the H/F coils are controlled through the third detuning circuit 122 to reduce residual interference and shielding effect caused by copper components in other array loops. By designing multiple independent detuning circuits to control the working states of multiple nuclide coils in a one-to-one manner, the interference between the nuclides of the inner and outer coils is reduced. When a Na array (a first sub-coil array) and an H/F dual-tuned array (a second coil array) work simultaneously, a P array (a second sub-coil array) is detuned. When the P array works, the Na array and the H/F dual-tuned array are detuned to reduce the electromagnetic interference between the P array and the H/F/N array. To decouple the P array and the H/F/Na array, three active detuning circuits are inserted in each loop of an array to reduce residual interference and shielding effect caused by copper components in other array loops. In this embodiment, the values of elements in each coil can be adjusted according to actual conditions and are not limited in this embodiment.

The front-end module 2 is connected to the coil module 1 and configured to generate a nuclear magnetic test signal and collect an induction signal.

In this embodiment, the front-end module 2 is configured to connect to an external radio frequency signal generator. By inputting a nuclear magnetic test signal and using, for example, a quadrature coupler to perform phase deviation on the nuclear magnetic test signal, the nuclear magnetic test signal is divided into multiple radio frequency signals with different phases. Multiple nuclide signals can be simultaneously or non-simultaneously emitted to perform nuclear magnetic resonance imaging.

This embodiment discloses a quad-core radio-frequency coil circuit. The quad-core radio-frequency coil circuit includes a coil module and a front-end module. The coil module is configured to receive a nuclear magnetic test signal and, according to the nuclear magnetic test signal, generate an induction signal. The front-end module is connected to the coil module and configured to generate the nuclear magnetic test signal and collect the induction signal. In this embodiment of the present application, a four-core radio-frequency coil circuit is designed through using a double-layer nested structure. On the basis of high cooperation with a multi-frequency and multi-channel electronic and timing control system, the four-core radio-frequency coil circuit can simultaneously or non-simultaneously emit multiple nuclide signals to perform nuclear magnetic resonance imaging. Thus, the problems of interaction and electromagnetic interference between different nuclides are solved, and multi-channel, multi-frequency, and high-uniformity radio-frequency excitation and high sensitivity signal collection are implemented.

Embodiment Two

Figure 19:
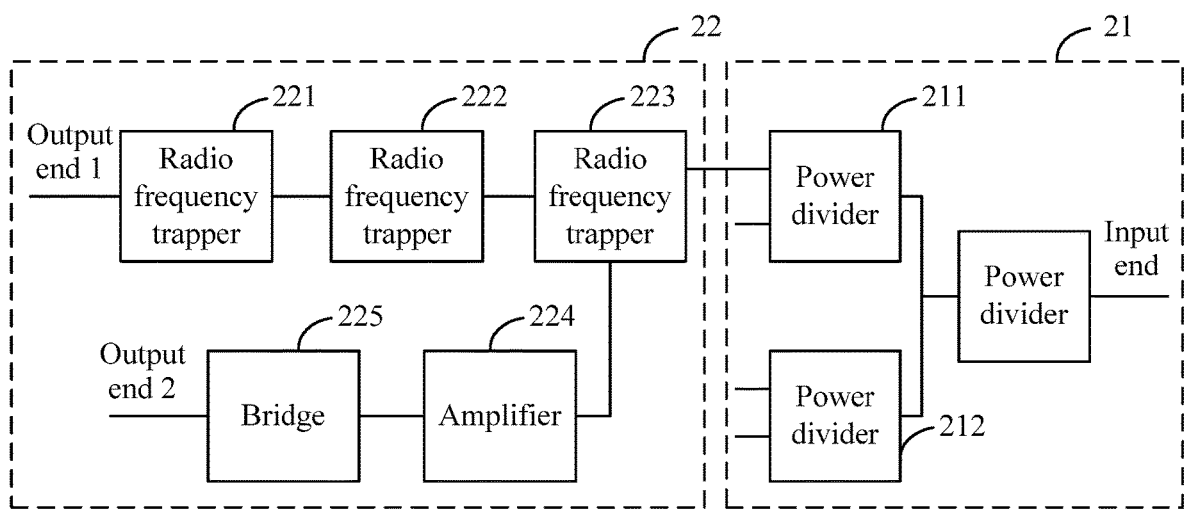
FIG. 19 is a circuit diagram of a front-end module according to embodiment two of the present application.

This embodiment describes the structure of a front-end module on the basis of the embodiment one. FIG. 19 is a circuit diagram of a front-end module according to embodiment two. A front-end module 2 includes a power division module 21 and a signal driver module 22.

The power division module 21 is connected to the signal driver module 22. The power division module 21 is configured to divide a nuclear magnetic test signal into multiplex test signals.

In this embodiment, the power division module 21 includes three 1:2 power dividers which are respectively a power divider 211, a power divider 212, and a power divider 213. The input end of the power division module 21 is configured to connect to an external signal generator. A high-power output signal input from the outside is divided into four signals by three 1:2 power dividers. The four signals are correspondingly input to different coil units in a coil module 1. The power division module 21 is configured to cooperate to implement the amplitude and phase regulation of excitation sources of multiple channels, to separate four signals, and to finally implement amplitude change and phase modulation of the excitation sources of multiple channels.

The signal driver module 22 is connected to the coil module 1. The signal driver module 22 is configured to input multiplex test signals into the coil module 1.

In this embodiment, four signal driver modules 22 are connected to the power division module 21 to generate four signals. The coaxial cable of each coil is connected to three radio frequency trappers (radio frequency trapper 221, radio frequency trapper 222, and radio frequency trapper 223) of different frequencies. A radio frequency trapper corresponding to the working frequency of a coil is connected at a position close to the direction of the coil. Another two radio frequency trappers are connected after the radio frequency trapper corresponding to the working frequency of a coil. A test signal is input to the coil module 1 through an output end 1. A weak magnetic resonance voltage signal received from the coil is amplified by an amplifier 224 and is divided into two signals by a bridge 225. The signals are transmitted to a spectrometer through a hospital bed to complete image reconstruction and display the magnetic resonance imaging result.

Figure 20:
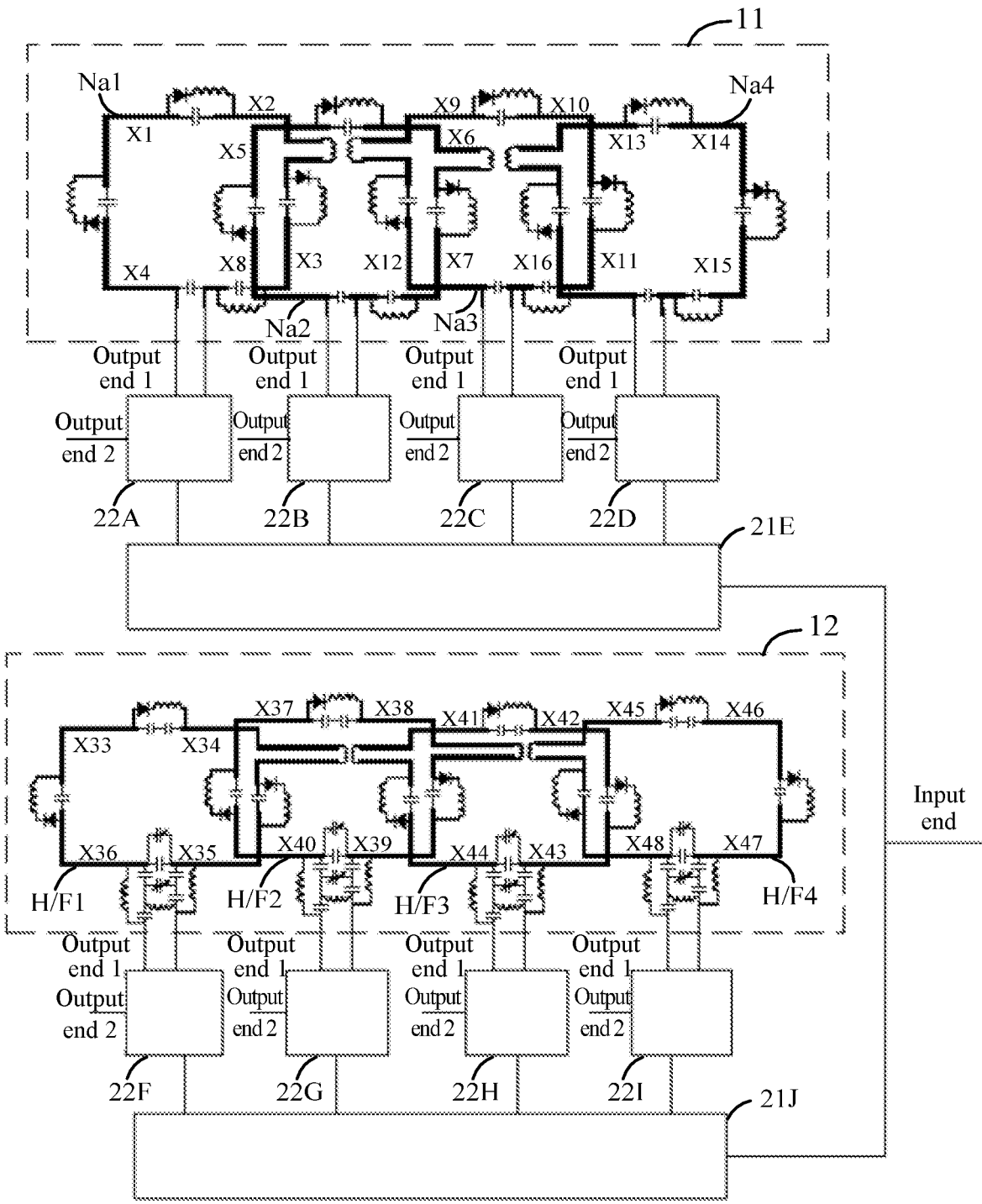
FIG. 20 is a circuit diagram of a quad-core radio-frequency coil circuit according to embodiment two of the present application.

Referring to FIG. 20, FIG. 20 is a circuit diagram of a quad-core radio-frequency coil circuit according to this embodiment. A first sub-coil array 11a is connected to four signal driver modules 22A, 22B, 22C and 22D. Four signal driver modules 22A, 22B, 22C and 22D are connected to a power division module 21E. The power division module 21E is connected to an external signal input end. A second coil array 12 is connected to four signal driver modules 22F, 22G, 22H and 22I. The four signal driver modules 22F, 22G, 22H and 22I are connected to a power division module 21J. The power division module 21J is connected to the external signal input end. A preset nuclear magnetic signal is divided into multiple signals of different phase differences by a power division module and input to the first sub-coil array 11a and the second coil array 12 by the signal input end. The signals are input to an external display device through detected feedback signals so that the nuclear magnetic detection result can be observed. In an alternative embodiment, the first sub-coil array 11a and the second coil array may not be connected to the same signal input end. This may be selected according to the actual application.

The connection relationship between a second sub-coil array and a signal driver module is similar to that between a first sub-coil array and a signal driver module, and details are not described herein.

This embodiment discloses a quad-core radio-frequency coil circuit. The quad-core radio-frequency coil circuit includes a coil module and a front-end module. The coil module is configured to receive a nuclear magnetic test signal and, according to the nuclear magnetic test signal, generate an induction signal. The front-end module is connected to the coil module and configured to generate the nuclear magnetic test signal and collect the induction signal. In this embodiment of the present application, a four-core radio-frequency coil circuit is designed through using a double-layer nested structure. On the basis of high cooperation with a multi-frequency and multi-channel electronic and timing control system, the four-core radio-frequency coil circuit can simultaneously or non-simultaneously emit multiple nuclide signals to perform nuclear magnetic resonance imaging. Thus, the problems of interaction and electromagnetic interference between different nuclides are solved, and multi-channel, multi-frequency, and high-uniformity radio-frequency excitation and high sensitivity signal collection are implemented.

What is claimed is:

1. A quad-core radio frequency coil circuit, comprising:
   a coil module configured to receive a nuclear magnetic test signal and generate an induction signal according to the nuclear magnetic test signal; and
   a front-end module connected to the coil module and configured to generate the nuclear magnetic test signal and collect the induction signal;
   wherein the coil module comprises a first coil array and a second coil array of two combined nuclides, and a center position of the first coil array coincides with a center position of the second coil array, the first coil array and the second coil array are designed through using a double-layer nested structure;

wherein the first coil array comprises a first sub-coil array of a first nuclide and a second sub-coil array of a second nuclide, wherein the two combined nuclides, the first nuclide and the second nuclide are different from each other;

the first sub-coil array comprises a plurality of first coil units, the second sub-coil array comprises a plurality of second coil units, and the second coil array comprises a plurality of third coil units, wherein each of the plurality of first coil units, each of the plurality of second coil units and each of the plurality of third coil units respectively transmit different nuclide signals, a center line of each of the plurality of second coil units coincides with a center line of a corresponding third coil unit, a center line of each of the plurality of first coil units is shifted relative to a center line of the corresponding third coil unit.

2. The quad-core radio-frequency coil circuit according to claim 1, the plurality of first coil units are superimposed based on a first preset phase difference; the plurality of second coil units are superimposed based on a second preset phase difference; the plurality of third coil units are superimposed based on a third preset phase difference.

3. The quad-core radio-frequency coil circuit according to claim 2, wherein a first coil unit of the plurality of first coil units comprises a first interface circuit and a first detuning circuit, the first detuning circuit is connected to the first interface circuit, and the first interface circuit is connected to the front-end module.

4. The quad-core radio-frequency coil circuit according to claim 3, wherein the first interface circuit comprises an input end IN1, an input end IN2, a capacitor C1, a capacitor C2, and an inductor L1, wherein the input end IN1 is connected to a first end of the capacitor C1, a second end of the capacitor C1 is connected to a first end of the capacitor C2, a second end of the capacitor C2 is connected to a first end of the inductor L1, a second end of the inductor L1 is connected to the first end of the capacitor C2, and the input end IN2 is connected to the second end of the capacitor C1.

5. The quad-core radio-frequency coil circuit according to claim 3, wherein the first detuning circuit comprises an inductor L2, an inductor L3, an inductor L4, an inductor L5, a capacitor C3, a capacitor C4, a capacitor C5, a diode D1, a diode D2, and a diode D3, wherein a first end of the inductor L2 is connected to a first end of the capacitor C3, a second end of the inductor L2 is connected to a negative electrode of the diode D1, a positive electrode of the diode D1 is connected to a second end of the capacitor C3, a second end of the capacitor C4 is connected to the first end of the capacitor C3, a positive electrode of the diode D2 is connected to the second end of the capacitor C4, a negative electrode of the diode D2 is connected to a second end of the inductor L3, a first end of the inductor L3 is connected to a first end of the capacitor C4, a positive electrode of the diode D3 is connected to a second end of the capacitor C5, a negative electrode of the diode D3 is connected to a second end of the inductor L4, a first end of the inductor L4 is connected to a first end of the capacitor C5, a first end of the inductor L5 is connected to the second end of the capacitor C5, and a second end of the inductor L5 is connected to the first end of the capacitor C4; alternatively, a first end of the inductor L2 is connected to a first end of the capacitor C3, a second end of the inductor L2 is connected to a negative electrode of the diode D1, a positive electrode of the diode D1 is connected to a second end of the capacitor C3, a second end of the capacitor C4 is connected to the second end of the capacitor C3, a positive electrode of the diode D2 is connected to a first end of the capacitor C4, a negative electrode of the diode D2 is connected to a second end of the inductor L3, a first end of the inductor L3 is connected to the second end of the capacitor C4, a positive electrode of the diode D3 is connected to a second end of the capacitor C5, a negative electrode of the diode D3 is connected to a second end of the inductor L4, a first end of the inductor L4 is connected to a first end of the capacitor C5, a first end of the inductor L5 is connected to the first end of the capacitor C5, and a second end of the inductor L5 is connected to the first end of the capacitor C4.

6. The quad-core radio-frequency coil circuit according to claim 2, wherein a second coil unit of the plurality of second coil units comprises a second interface circuit and a second detuning circuit, the second detuning circuit is connected to the second interface circuit, and the second interface circuit is connected to the front-end module.

7. The quad-core radio-frequency coil circuit according to claim 6, wherein the second interface circuit comprises an input end IN1, an input end IN2, a capacitor C6, a capacitor C7, and an inductor L6, wherein the input end IN1 is connected to a first end of the capacitor C6, a second end of the capacitor C6 is connected to a first end of the capacitor C7, a second end of the capacitor C7 is connected to a first end of the inductor L6, a second end of the inductor L6 is connected to the first end of the capacitor C7, and the input end IN2 is connected to the second end of the capacitor C6.

8. The quad-core radio-frequency coil circuit according to claim 6, wherein the second detuning circuit comprises an inductor L7, an inductor L8, an inductor L9, an inductor L10, a capacitor C8, a capacitor C9, a capacitor C10, a diode D4, a diode D5, and a diode D6, wherein a first end of the inductor L7 is connected to a first end of the capacitor C8, a second end of the inductor L7 is connected to a negative electrode of the diode D4, a positive electrode of the diode D4 is connected to a second end of the capacitor C8, a second end of the capacitor C9 is connected to the first end of the capacitor C8, a positive electrode of the diode D5 is connected to the second end of the capacitor C9, a negative electrode of the diode D5 is connected to a second end of the inductor L8, a first end of the inductor L8 is connected to a first end of the capacitor C9, a positive electrode of the diode D6 is connected to a second end of the capacitor C10, a negative electrode of the diode D6 is connected to a second end of the inductor L9, a first end of the inductor L9 is connected to a first end of the capacitor C10, a first end of the inductor L10 is connected to the second end of the capacitor C10, and a second end of the inductor L10 is connected to the first end of the capacitor C9; alternatively, a first end of the inductor L7 is connected to a first end of the capacitor C8, a second end of the inductor L7 is connected to a negative electrode of the diode D4, a positive electrode of the diode D4 is connected to a second end of the capacitor C8, a second end of the capacitor C9 is connected to the second end of the capacitor C8, a positive electrode of the diode D5 is connected to a first end of the capacitor C9, a negative electrode of the diode D5 is connected to a second end of the inductor L8, a first end of the inductor L8 is connected to the second end of the capacitor C9, a positive electrode of the diode D6 is connected to a second end of the capacitor C10, a negative electrode of the diode D6 is connected to a second end of the inductor L9, a first end of the inductor L9 is connected to a first end of the capacitor C10, a first end of the inductor L10 is connected to the first end of the capacitor C10, and a second end of the inductor L10 is connected to the first end of the capacitor C9.

9. The quad-core radio-frequency coil circuit according to claim 2, wherein a third coil unit of the plurality of third coil units comprises a third interface circuit and a third detuning circuit, the third detuning circuit is connected to the third interface circuit, and the third interface circuit is connected to the front-end module.

10. The quad-core radio-frequency coil circuit according to claim 9, wherein the third interface circuit comprises an input end IN1, an input end IN2, a capacitor C11, a capacitor C12, a capacitor C13, a capacitor C14, a capacitor C15, a variable capacitor B1, a variable capacitor B2, an inductor L11, an inductor L12, and an inductor L13, wherein the input end IN1 is connected to a first end of the capacitor C11, a second end of the capacitor C11 is connected to a first end of the capacitor C12, a first end of the inductor L13 is connected to a second end of the capacitor C12, a second end of the inductor L13 is connected to the first end of the capacitor C11, a first end of the capacitor C13 is connected to the second end of the capacitor C12, a second end of the capacitor C13 is connected to a first end of the capacitor C14, a second end of the capacitor C14 is connected to a first end of the capacitor C15, a second end of the capacitor C15 is connected to the input end IN2, a first end of the inductor L12 is connected to the second end of the capacitor C11, a second end of the inductor L12 is connected to the second end of the capacitor C15, a first end of the inductor L11 is connected to the first end of the capacitor C14, a second end of the inductor L11 is connected to the second end of the capacitor C15, a first end of the variable capacitor B1 is connected to the first end of the capacitor C13, a second end of the variable capacitor B1 is connected to the second end of the capacitor C13, a first end of the variable capacitor B2 is connected to the first end of the capacitor C12, and a second end of the variable capacitor B2 is connected to the second end of the capacitor C15.

11. The quad-core radio-frequency coil circuit according to claim 9, wherein the third detuning circuit comprises a capacitor C16, a capacitor C17, a capacitor C18, a capacitor C19, an inductor L14, an inductor L15, an inductor L16, an inductor L17, a diode D7, a diode D8, and a diode D9, wherein a first end of the inductor L16 is connected to a first end of the capacitor C16, a second end of the inductor L16 is connected to a negative electrode of the diode D7, a positive electrode of the diode D7 is connected to a second end of the capacitor C16, a second end of the capacitor C17 is connected to the first end of the capacitor C16, a first end of the capacitor C17 is connected to a second end of the capacitor C18, a positive electrode of the diode D8 is connected to the second end of the capacitor C17, a negative electrode of the diode D8 is connected to a second end of the inductor L14, a first end of the inductor L14 is connected to a first end of the capacitor C18, a positive electrode of the diode D9 is connected to a second end of the capacitor C19, a negative electrode of the diode D9 is connected to a second end of the inductor L15, a first end of the inductor L15 is connected to a first end of the capacitor C19, a first end of the inductor L17 is connected to the first end of the capacitor C18, and a second end of the inductor L17 is connected to the second end of the capacitor C19; alternatively, a first end of the inductor L16 is connected to a first end of the capacitor C16, a second end of the inductor L16 is connected to a negative electrode of the diode D7, a positive electrode of the diode D7 is connected to a second end of the capacitor C16, a second end of the capacitor C18 is connected to the second end of the capacitor C16, a first end of the capacitor C17 is connected to a first end of the capacitor C18, a positive electrode of the diode D8 is connected to a second end of the capacitor C17, a negative electrode of the diode D8 is connected to a second end of the inductor L14, a first end of the inductor L14 is connected to the second end of the capacitor C18, a positive electrode of the diode D9 is connected to a second end of the capacitor C19, a negative electrode of the diode D9 is connected to a second end of the inductor L15, a first end of the inductor L15 is connected to a first end of the capacitor C19, a first end of the inductor L17 is connected to the second end of the capacitor C17, and a second end of the inductor L17 is connected to the first end of the capacitor C19.

12. The quad-core radio-frequency coil circuit according to claim 1, wherein the front-end module comprises a power division module and a signal driver module, the power division module is connected to the signal driver module, the signal driver module is connected to the coil module, the power division module is configured to divide the nuclear magnetic test signal into multiplex test signals, and the signal driver module is configured to input the multiplex test signals into the coil module.

* * * * *